(12) United States Patent
Follmann et al.

(10) Patent No.: US 9,150,580 B2
(45) Date of Patent: Oct. 6, 2015

(54) SUBSTITUTED IMIDAZOPYRIDINES AND THE USE THEREOF

(75) Inventors: Markus Follmann, Köln (DE);
Johannes-Peter Stasch, Solingen (DE);
Gorden Redlich, Bochum (DE);
Alexander Straub, Wuppertal (DE);
Jens Ackerstaff, Düsseldorf (DE); Nils Griebenow, Dormagen, DE (US);
Andreas Knorr, Erkrath (DE); Frank Wunder, Wuppertal (DE); Volkhart Min-Jian Li, Velbert (DE)

(73) Assignees: BAYER INTELLECTUAL PROPERTY GMBH, Monheim (DE);
BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 14/115,871

(22) PCT Filed: May 2, 2012

(86) PCT No.: PCT/EP2012/058048
§ 371 (c)(1),
(2), (4) Date: Jan. 8, 2014

(87) PCT Pub. No.: WO2012/152630
PCT Pub. Date: Nov. 15, 2012

(65) Prior Publication Data
US 2014/0113900 A1    Apr. 24, 2014

(30) Foreign Application Priority Data
May 6, 2011    (DE) .......................... 10 2011 075 398

(51) Int. Cl.
| | | |
|---|---|---|
| *C07D 487/04* | (2006.01) | |
| *A61K 31/5025* | (2006.01) | |
| *A61K 31/53* | (2006.01) | |
| *A61K 45/06* | (2006.01) | |

(52) U.S. Cl.
CPC .......... *C07D 487/04* (2013.01); *A61K 31/5025* (2013.01); *A61K 31/53* (2013.01); *A61K 45/06* (2013.01)

(58) Field of Classification Search
CPC .................................................... C07D 487/04
See application file for complete search history.

(56) References Cited

U.S. PATENT DOCUMENTS

| | | |
|---|---|---|
| 6,180,656 B1 | 1/2001 | Fürstner et al. |
| 6,743,798 B1 | 6/2004 | Straub et al. |
| 7,173,037 B2 | 2/2007 | Alonso-Alija et al. |
| 8,309,551 B2 | 11/2012 | Schirok et al. |

FOREIGN PATENT DOCUMENTS

| | | |
|---|---|---|
| WO | 2010065275 | 6/2010 |
| WO | 2011119518 | 3/2011 |

OTHER PUBLICATIONS

Badesch et al., "Prostanoid Therapy for Pulmonary Arterial Hypertension," J. Am. College of Cardiology, 2004, 43(12) Supp S, 5S-61S.
Glass et al., "Stimulation of Human Platelet Guanylate Cyclase by Fatty Acids," J. Biol. Chem., Feb. 25, 1977, 252 (4):1279-1285.
Ko et al., "YC-1, a Novel Activator of Platelet Guanylate Cyclase," Blood, Dec. 1994, 84(12):4226-4233.
Mülsch et al., "Effect of YC-1, an NO-independent, superoxide-sensitive stimulator of soluble guanylyl cyclase, on smooth muscle responsiveness to nitrovasodilators," Brit. J. Pharm., 1997, 120:681-689.
Pettibone et al., "A Structurally Novel Stimulator of Guanylate Cyclase with Long-Lasting Hypotensive Activity in the Dog," Euro. J. of Pharmacology, 1985, 116:307-312.
Yu et al., "Vasorelaxant Effect of Isoliquiritigenin, A novel soluble guanylate cyclase activator, in rat aorta," Brit. J. of Pharmacology, 1995, 114:1587-1594.

*Primary Examiner* — Brian McDowell
(74) *Attorney, Agent, or Firm* — Buchanan Ingersoll & Rooney PC

(57) ABSTRACT

The present application relates to novel substituted imidazopyridazines having the following formula (I):

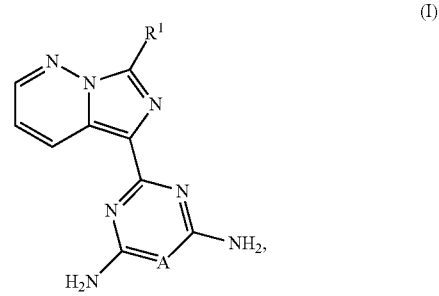

to processes for their preparation, to their use, alone or in combinations, for the treatment and/or prophylaxis of diseases and to their use for production of medicaments for the treatment and/or prophylaxis of diseases, especially for the treatment and/or prophylaxis of cardiovascular disorders.

4 Claims, No Drawings

SUBSTITUTED IMIDAZOPYRIDINES AND THE USE THEREOF

The present application relates to novel substituted imidazopyridazines, to processes for their preparation, to their use, alone or in combinations, for the treatment and/or prophylaxis of diseases and to their use for production of medicaments for the treatment and/or prophylaxis of diseases, especially for the treatment and/or prophylaxis of cardiovascular disorders.

One of the most important cellular transmission systems in mammalian cells is cyclic guanosine monophosphate (cGMP). Together with nitrogen monoxide (NO), which is released from the endothelium and transmits hormonal and mechanical signals, it forms the NO/cGMP system. Guanylate cyclases catalyse the biosynthesis of cGMP from guanosine triphosphate (GTP). The representatives of this family known to date can be divided into two groups either according to structural features or according to the type of ligands: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory site. This is of central importance for the activation mechanism. NO can bind to the iron atom of heme and thus markedly increase the activity of the enzyme. Heme-free preparations cannot, by contrast, be stimulated by NO. Carbon monoxide (CO) is also able to bind to the central iron atom of heme, but the stimulation by CO is much less than that by NO.

By forming cGMP, and owing to the resulting regulation of phosphodiesterases, ion channels and protein kinases, guanylate cyclase plays an important role in various physiological processes, in particular in the relaxation and proliferation of smooth muscle cells, in platelet aggregation and platelet adhesion and in neuronal signal transmission, and also in disorders which are based on a disruption of the abovementioned processes. Under pathophysiological conditions, the NO/cGMP system can be suppressed, which can lead, for example, to hypertension, platelet activation, increased cell proliferation, endothelial dysfunction, atherosclerosis, angina pectoris, heart failure, myocardial infarction, thromboses, stroke and sexual dysfunction.

Owing to the expected high efficiency and low level of side effects, a possible NO-independent treatment for such disorders by targeting the influence of the cGMP signal pathway in organisms is a promising approach.

Therapeutic stimulation of soluble guanylate cyclase has to date been accomplished using exclusively compounds such as organic nitrates, the effect of which is based on NO. The latter is formed by bioconversion and activates soluble guanylate cyclase by attack at the central iron atom of heme. In addition to the side effects, the development of tolerance is one of the crucial disadvantages of this mode of treatment.

In recent years, some substances have been described which stimulate soluble guanylate cyclase directly, i.e. without prior release of NO, such as, for example 3-(5'-hydroxymethyl-2'-furyl)-1-benzylindazole [YC-1; Wu et al., Blood 84 (1994), 4226; Mülsch et al., Brit. J. Pharmacol. 120 (1997), 681], fatty acids [Goldberg et al., J. Biol. Chem. 252 (1977), 1279], diphenyliodonium hexafluorophosphate [Pettibone et al., Eur. J. Pharmacol. 116 (1985), 307], isoliquiritigenin [Yu et al., Brit. J. Pharmacol. 114 (1995), 1587] and various substituted pyrazole derivatives (WO 98/16223).

As stimulators of soluble guanylate cyclase, WO 00/06569 discloses fused pyrazole derivatives, and WO 03/095451 carbamate-substituted 3-pyrimidinylpyrazolopyridines. WO 2008/031513 describes inter alia substituted imidazopyridines and imidazopyrimidines as stimulators of soluble guanylate cyclase. 4-Amino-5,5-dimethyl-5,7,dihydro-6H-pyrrolo[2,3-d]pyrimidones having imidazopyridine and -pyrimidine substituents are disclosed as sGC activators in WO 2010/065275.

It was an object of the present invention to provide novel substances which act as potent stimulators of soluble guanylate cyclase.

The present invention provides compounds of the general formula (I)

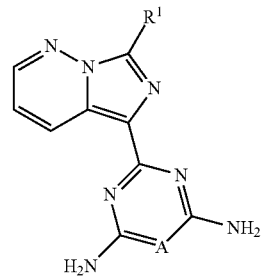

(I)

in which
R$^1$ is (C$_1$-C$_6$)-alkyl or benzyl,
where (C$_1$-C$_6$)-alkyl is substituted by one trifluoromethyl substituent,
where (C$_1$-C$_6$)-alkyl may be substituted by 1 to 3 fluorine substituents,
and
where benzyl is substituted by 1 to 3 fluorine substituents,
A is N or C—N(R$^2$)—C(=O)—R$^3$,
where
R$^2$ is hydrogen, (C$_1$-C$_4$)-alkyl or benzyl,
in which (C$_1$-C$_4$)-alkyl and benzyl may be substituted by 1 or 2 substituents independently of one another selected from the group consisting of fluorine and trifluoromethyl,
R$^3$ is (C$_1$-C$_6$)-alkyl, (C$_3$-C$_7$)-cycloalkyl, (C$_1$-C$_6$)-alkoxy or (C$_3$-C$_7$)-cycloalkoxy,
in which (C$_1$-C$_6$)-alkyl and (C$_1$-C$_6$)-alkoxy may be substituted by 1 or 2 substituents independently of one another selected from the group consisting of fluorine and trifluoromethyl,
or
R$^2$ and R$^3$ together with the atoms to which they are attached form a 4- to 7-membered heterocycle,
in which the 4- to 7-membered heterocycle may be substituted by 1 or 2 (C$_1$-C$_4$)-alkyl substituents,
and the N-oxides, salts, solvates, salts of N-oxides and solvates of the N-oxides or salts thereof.

Compounds according to the invention are the compounds of the formula (I) and their salts, solvates and solvates of the salts, the compounds, comprised by formula (I), of the formulae mentioned below and their salts, solvates and solvates of the salts and the compounds comprised by formula (I), mentioned below as embodiments, and their salts, solvates and solvates of the salts, if the compounds, comprised by formula (I), mentioned below are not already salts, solvates and solvates of the salts.

In the context of the present invention, preferred salts are physiologically acceptable salts of the compounds according to the invention. Also encompassed are salts which are not themselves suitable for pharmaceutical applications but can be used, for example, for isolation or purification of the compounds according to the invention.

Physiologically acceptable salts of the compounds according to the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, formic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the invention, solvates refer to those forms of the compounds according to the invention which, in the solid or liquid state, form a complex by coordination with solvent molecules. Hydrates are a specific form of solvates in which the coordination is with water. Solvates preferred in the context of the present invention are hydrates.

The compounds according to the invention may, depending on their structure, exist in different stereoisomeric forms, i.e. in the form of configurational isomers or else optionally as conformational isomers (enantiomers and/or diastereomers, including those in the case of atropisomers). The present invention therefore encompasses the enantiomers and diastereomers, and the respective mixtures thereof. The stereoisomerically uniform constituents can be isolated from such mixtures of enantiomers and/or diastereomers in a known manner; chromatography processes are preferably used for this, in particular HPLC chromatography on an achiral or chiral phase.

Where the compounds according to the invention can occur in tautomeric forms, the present invention encompasses all the tautomeric forms.

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass than that which occurs usually or predominantly in nature. Examples of isotopes which can be incorporated into a compound according to the invention are those of hydrogen, carbon, nitrogen, oxygen, phosphorus, sulfur, fluorine, chlorine, bromine and iodine, such as $^{2}H$ (deuterium), $^{3}H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Particular isotopic variants of a compound according to the invention, such as, more particularly, those in which one or more radioactive isotopes have been incorporated, may be of benefit, for example, for the study of the mechanism of action or of the active compound distribution in the body; due to the comparative ease of preparability and detectability, compounds labeled particularly with $^{3}H$ or $^{14}C$ isotopes are suitable for this purpose. Furthermore, the incorporation of isotopes, for example of deuterium, can lead to particular therapeutic advantages as a consequence of greater metabolic stability of the compound, for example an extension of the half-life in the body or a reduction in the active dose required; such modifications of the compounds according to the invention may therefore, in some cases, also constitute a preferred embodiment of the present invention. Isotopic variants of the compounds according to the invention can be prepared by the processes known to those skilled in the art, for example by the methods described below and the procedures described in the working examples, by using corresponding isotopic modifications of the respective reagents and/or starting compounds.

Moreover, the present invention also encompasses prodrugs of the compounds according to the invention. Here, the term "prodrugs" refers to compounds which for their part can be biologically active or inactive, but are converted (for example metabolically or hydrolytically) into compounds according to the invention during their dwell time in the body.

In the context of the present invention, the substituents, unless specified otherwise, are each defined as follows:

Alkyl in the context of the invention is a linear or branched alkyl radical having 1 to 6 carbon atoms. Preference is given to a linear or branched alkyl radical having 1 to 4 carbon atoms. The following may be mentioned by way of example and with preference: methyl, ethyl, n-propyl, isopropyl, n-butyl, isobutyl, 1-methylpropyl, tert-butyl, n-pentyl, 2-methylbutyl, 2-ethylpropyl and n-hexyl.

Cycloalkyl in the context of the invention is a monocyclic saturated carbocycle having 3 to 7 ring carbon atoms. The following may be mentioned by way of example and with preference: cyclopropyl, cyclobutyl, cyclopentyl, cyclohexyl and cycloheptyl.

Alkoxy in the context of the invention is a linear or branched alkoxy radical having 1 to 6 carbon atoms. Preference is given to a linear or branched alkoxy radical having 1 to 4 carbon atoms. The following may be mentioned by way of example and with preference: methoxy, ethoxy, n-propoxy, isopropoxy, 1-methylpropoxy, n-butoxy, isobutoxy and tert-butoxy.

Cycloalkoxy in the context of the invention is a monocyclic saturated carbocycle which has 3 to 7 carbon atoms and is bonded via an oxygen atom. The following may be mentioned by way of example and with preference: cyclopropyloxy, cyclobutyloxy, cyclopentyloxy, cyclohexyloxy and cycloheptyloxy.

Heterocycle in the context of the invention is a saturated heterocycle having a total of 4 to 7 ring atoms, which contains one or two ring heteroatoms from the group consisting of N, O and S and is substituted by an oxo group. The following may be mentioned by way of example: pyrrolidinonyl, oxazolidinonyl, piperidinonyl, piperazinonyl, morpholinonyl and thiomorpholinonyl. Preference is given to pyrrolidinonyl and oxazolidinonyl.

Halogen in the context of the invention is fluorine, chlorine, bromine and iodine.

An oxo group in the context of the invention is an oxygen atom bonded via a double bond to a carbon atom.

When radicals in the compounds according to the invention are substituted, the radicals, unless specified otherwise, may be mono- or polysubstituted. In the context of the present invention, all radicals which occur more than once are defined independently of one another. Substitution by one, two or three identical or different substituents is preferred.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progress of such states and/or the symptoms of such states. The term "therapy" is understood here to be synonymous with the term "treatment".

The terms "prevention", "prophylaxis" or "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

Preference is given in the context of the present invention to compounds of the formula (I) in which
  $R^1$ is 3,3,4,4,4-pentafluorobut-1-yl or 2-fluorobenzyl,
  A is N or C—N($R^2$)—C(=O)—$R^3$,
  where
    $R^2$ is hydrogen, methyl, ethyl, isopropyl or benzyl,
      in which methyl, ethyl and benzyl may be substituted by 1 or 2 substituents independently of one another selected from the group consisting of fluorine and trifluoromethyl,
    $R^3$ is ($C_1$-$C_4$)-alkyl, ($C_3$-$C_5$)-cycloalkyl, ($C_1$-$C_4$)-alkoxy or ($C_3$-$C_5$)-cycloalkoxy,
      in which ($C_1$-$C_4$)-alkyl and ($C_1$-$C_4$)-alkoxy may be substituted by 1 or 2 substituents independently of one another selected from the group consisting of fluorine and trifluoromethyl,
    or
    $R^2$ and $R^3$ together with the atoms to which they are attached form a 5- or 6-membered heterocycle,
      in which the 5- or 6-membered heterocycle may be substituted by 1 or 2 methyl substituents,
  and their salts, solvates and solvates of the salts.

Particular preference is given in the context of the present invention to compounds of the formula (I) in which
  $R^1$ is 2-fluorobenzyl,
  A is C—N($R^2$)—C(=O)—$R^3$,
  where
    $R^2$ is hydrogen, methyl, ethyl or 2,2,2-trifluoroethyl,
    $R^3$ is ($C_1$-$C_4$)-alkoxy, cyclobutoxy or cyclopentoxy,
      in which ($C_1$-$C_4$)-alkoxy may be substituted by 1 or 2 substituents independently of one another selected from the group consisting of fluorine and trifluoromethyl,
    or
    $R^2$ and $R^3$ together with the atoms to which they are attached form a pyrrolidinonyl or oxazolidinonyl ring,
  and their salts, solvates and solvates of the salts.

Preference is also given in the context of the present invention to compounds of the formula (I) in which
  $R^1$ is 2-fluorobenzyl,
  and their salts, solvates and solvates of the salts.

The individual radical definitions specified in the particular combinations or preferred combinations of radicals are, independently of the particular combinations of the radicals specified, also replaced as desired by radical definitions of other combinations.

Particular preference is given to combinations of two or more of the preferred ranges mentioned above.

The invention further provides a process for preparing the compounds of the formula (I) according to the invention, characterized in that

[A] a compound of the formula (II)

(II)

in which $R^1$ has the meaning given above is reacted in an inert solvent in the presence of a suitable base with 1-cyanoguanidine to give a compound of the formula (I-A)

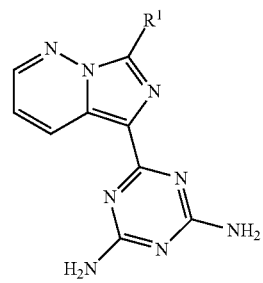

(I-A)

in which $R^1$ has the meaning given above, or

[B] a compound of the formula (III)

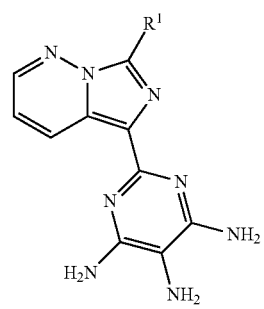

(III)

in which $R^1$ has the meaning given above, is reacted in an inert solvent in the presence of a suitable base with a compound of the formula (IV)

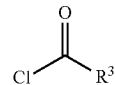

(IV)

in which $R^3$ has the meaning given above, to give a compound of the formula (I-B)

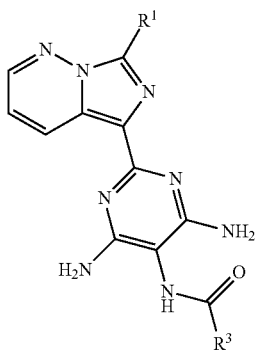

(I-B)

in which $R^1$ and $R^3$ each have the meanings given above,
or
[C] a compound of the formula (I-B) is converted in an inert solvent in the presence of a suitable base with a compound of the formula (V)

$$R^2—X^1 \quad (V)$$

in which $R^2$ has the meaning given above and
$X^1$ represents a suitable leaving group, for example mesylate, tosylate or halogen, in particular bromine or iodine, into a compound of the formula (I-C)

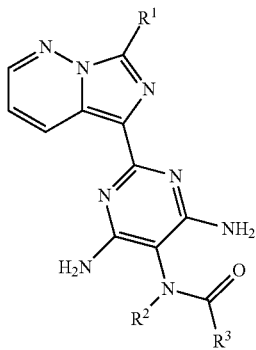

(I-C)

in which $R^1$, $R^2$ and $R^3$ each have the meanings given above,
and the resulting compounds of the formulae (I-A), (I-B) and (I-C) are, where appropriate, converted with the appropriate (i) solvents and/or (ii) acids or bases into their solvates, salts and/or solvates of the salts.

Inert solvents for the process step (II)→(I-A) are, for example, alcohols such as methanol, ethanol, n-propanol, isopropanol, n-butanol or tert-butanol, ethers such as diethyl ether, dioxane, tetrahydrofuran, glycol dimethyl ether or diethylene glycol dimethyl ether, halogenated hydrocarbons such as dichloromethane, trichloromethane, carbon tetrachloride, trichloroethylene or chlorobenzene, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), N-methylpyrrolidone (NMP), acetonitrile or else water. It is also possible to use mixtures of the solvents mentioned. Preference is given to DMSO.

Suitable bases for the process step (II)→(I-A) are alkali metal hydroxides such as, for example, lithium hydroxide, sodium hydroxide or potassium hydroxide, alkali metal carbonates such as lithium carbonate, sodium carbonate, potassium carbonate or cesium carbonate, alkali metal bicarbonates such as sodium bicarbonate or potassium bicarbonate, alkali metal alkoxides such as sodium methoxide or potassium methoxide, sodium ethoxide or potassium ethoxide or potassium tert-butoxide. Preference is given to sodium hydroxide.

The reaction (II)→(I-A) is generally carried out in a temperature range from +20° C. to +180° C., preferably at from +100° C. to +160° C. The reaction can be carried out at atmospheric, elevated or reduced pressure (for example from 0.5 to 5 bar).

Inert solvents for the process step (III)+(IV)→(I-B) are, for example, alcohols such as methanol, ethanol, n-propanol, isopropanol, n-butanol or tert-butanol, ethers such as diethyl ether, dioxane, tetrahydrofuran (THF), glycol dimethyl ether or diethylene glycol dimethyl ether, halogenated hydrocarbons such as dichloromethane, trichloromethane, carbon tetrachloride, trichloroethylene or chlorobenzene, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), N-methylpyrrolidone (NMP) or acetonitrile. It is also possible to use mixtures of the solvents mentioned. Preference is given to dichloromethane or THF.

Suitable bases for the process step (III)+(IV)→(I-B) are alkali metal hydrides such as sodium hydride, alkali metal hydroxides such as, for example, lithium hydroxide, sodium hydroxide or potassium hydroxide, alkali metal carbonates such as lithium carbonate, sodium carbonate, potassium carbonate or cesium carbonate, alkali metal bicarbonates such as sodium bicarbonate or potassium bicarbonate, alkali metal alkoxides such as sodium methoxide or potassium methoxide, sodium ethoxide or potassium ethoxide or potassium tert-butoxide, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to sodium hydride or pyridine.

The reaction (III)+(IV)→(I-B) is generally carried out in a temperature range from −10° C. to +30° C., preferably at from 0° C. to +20° C. The reaction can be carried out at atmospheric, elevated or reduced pressure (for example from 0.5 to 5 bar). The reaction is generally carried out at atmospheric pressure.

Inert solvents for the process step (I-B)+(V)→(I-C) are, for example, alcohols such as methanol, ethanol, n-propanol, isopropanol, n-butanol or tert-butanol, ethers such as diethyl ether, dioxane, tetrahydrofuran, glycol dimethyl ether or diethylene glycol dimethyl ether, halogenated hydrocarbons such as dichloromethane, trichloromethane, carbon tetrachloride, trichloroethylene or chlorobenzene, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), N-methylpyrrolidone (NMP), acetonitrile or else water. It is also possible to use mixtures of the solvents mentioned. Preference is given to THF.

Suitable bases for the process step (I-B)+(V)→(I-C) are alkali metal hydrides such as sodium hydride, alkali metal hydroxides such as, for example, lithium hydroxide, sodium hydroxide or potassium hydroxide, alkali metal carbonates such as lithium carbonate, sodium carbonate, potassium carbonate or cesium carbonate, alkali metal bicarbonates such as sodium bicarbonate or potassium bicarbonate, alkali metal alkoxides such as sodium methoxide or potassium methoxide, sodium ethoxide or potassium ethoxide or potassium tert-butoxide, amides such as sodium amide, lithium bis(trimethylsilyl)amide, sodium bis(trimethylsilyl)amide or potassium bis(trimethylsilyl)amide or lithium diisopropylamide, organometallic compounds such as butyllithium or phenyllithium, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to lithium bis(trimethylsilyl)amide or sodium hydride.

The reaction (I-B)+(V)→(I-C) is generally carried out in a temperature range from −10° C. to +30° C., preferably at from 0° C. to +20° C. The reaction can be carried out at atmospheric, elevated or reduced pressure (for example from 0.5 to 5 bar). The reaction is generally carried out at atmospheric pressure.

The preparation processes described can be illustrated by way of example by the following synthesis schemes (Schemes 1 and 2):

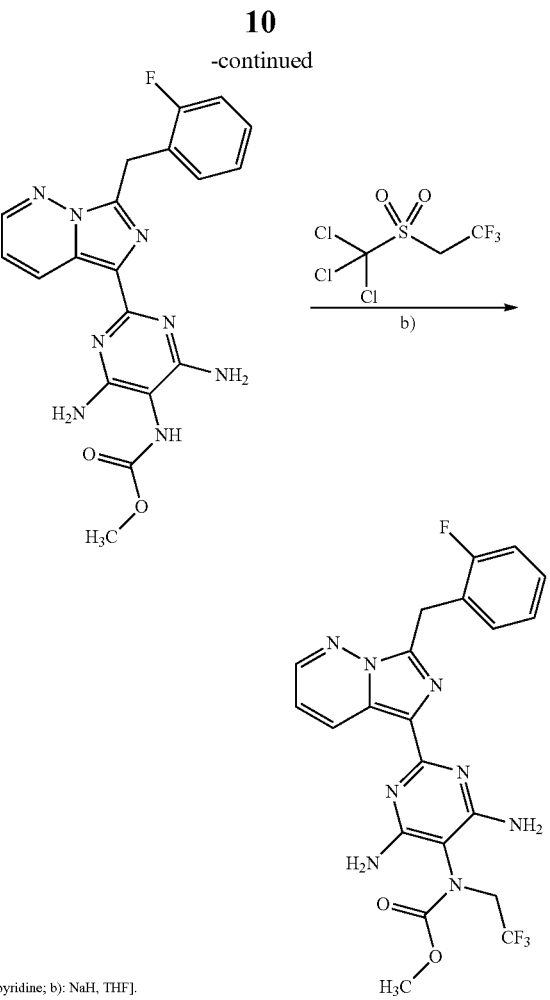

The compounds of the formulae (IV) and (V) are commercially available, known from the literature or can be prepared in analogy to literature processes.

The compounds of the formula (II) can be prepared by converting a compound of the formula (VI)

(VI)

in which R¹ has the meaning given above
in an inert solvent with a suitable brominating agent into a compound of the formula (VII)

(VII)

in which R¹ has the meaning given above
then reacting the latter in an inert solvent to give a compound of the formula (II)

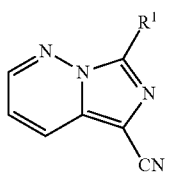
(II)

in which R¹ has the meaning given above.

The compound of the formula (III) can be prepared by converting a compound of the formula (II) in an inert solvent into a compound of the formula (VIII)

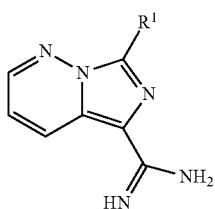
(VIII)

in which R¹ has the meaning given above then reacting the latter in an inert solvent in the presence of a suitable base with the compound of the formula (IX)

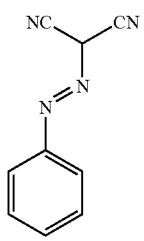
(IX)

to give a compound of the formula (X)

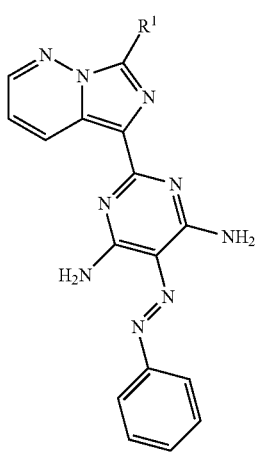
(X)

in which R¹ has the meaning given above and then reducing the latter in an inert solvent in the presence of a suitable reducing agent.

Suitable inert solvents for the bromination (VI)→(VII) are, for example, ethers such as diethyl ether, dioxane, tetrahydrofuran, glycol dimethyl ether or diethylene glycol dimethyl ether, halogenated hydrocarbons such as dichloromethane, trichloromethane, carbon tetrachloride, trichloroethylene or chlorobenzene, or other solvents such as dimethylformamide (DMF), dimethyl sulfoxide (DMSO), N,N'-dimethylpropyleneurea (DMPU), N-methylpyrrolidone (NMP), pyridine or acetonitrile. It is also possible to use mixtures of the solvents mentioned. Preference is given to dichloromethane.

A suitable brominating agent for process step (VI)→(VII) is elemental bromine with acetic acid, 1,3-dibromo-5,5-dimethylhydantoin and also, in particular, N-bromosuccinimide (NBS).

The bromination (VI)→(VII) is generally carried out in a temperature range from −10° C. to +50° C., preferably from 0° C. to +30° C. The conversion can be carried out at atmospheric, elevated or reduced pressure (for example in the range from 0.5 to 5 bar). The reaction is generally carried out at atmospheric pressure.

Inert solvents for the process step (VII)→(II) are, for example, ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), N-methylpyrrolidone (NMP), pyridine or acetonitrile. It is also possible to use mixtures of the solvents mentioned. Preference is given to DMSO.

The reaction (VII)→(II) is generally carried out in a temperature range from +20° C. to +180° C., preferably at from +100° C. to +160° C., optionally in a microwave. The reaction can be carried out at atmospheric, elevated or reduced pressure (for example from 0.5 to 5 bar). The reaction is generally carried out at atmospheric pressure.

The reaction (II)→(VIII) is carried out using methods known to the person skilled in the art in a two-step process initially with formation of the imino ester using sodium methoxide in methanol at from 0° C. to +40° C. and subsequent nucleophilic addition of an ammonia equivalent such as, for example, ammonia or ammonium chloride in acetic acid with formation of the amidine (VII) at from +50 to +150° C.

Inert solvents for the process step (VIII)+(IX)→(X) are alcohols such as methanol, ethanol, n-propanol, isopropanol, n-butanol or tert-butanol, ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), N-methylpyrrolidone (NMP), pyridine, acetonitrile or else water. It is also possible to use mixtures of the solvents mentioned. Preference is given to DMF.

Suitable bases for the process step (VIII)+(IX)→(X) are alkali metal hydroxides such as, for example, lithium hydroxide, sodium hydroxide or potassium hydroxide, alkali metal carbonates such as lithium carbonate, sodium carbonate, potassium carbonate or cesium carbonate, alkali metal bicarbonates such as sodium bicarbonate or potassium bicarbonate, alkali metal alkoxides such as sodium methoxide or potassium methoxide, sodium ethoxide or potassium ethoxide or potassium tert-butoxide, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to triethylamine.

The reaction (VIII)+(IX)→(X) is generally carried out in a temperature range of from +20° C. to +150° C., preferably at from +80° C. to +120° C., if appropriate in a microwave. The reaction can be carried out at atmospheric, elevated or reduced pressure (for example from 0.5 to 5 bar). The reaction is generally carried out at atmospheric pressure.

The compound of the formula (IX) can be prepared analogously to the literature L. F. Cavalieri, J. F. Tanker, A. Bendich, J. Am. Chem. Soc., 1949, 71, 533.

The reduction (X)→(III) is carried out in the presence of a suitable catalyst in an inert solvent in a temperature range of from +20° C. to +40° C. under hydrogen standard pressure.

Inert solvents for the reduction (X)→(III) are, for example, alcohols such as methanol, ethanol, n-propanol, isopropanol, n-butanol or tert-butanol, ethers such as diethyl ether, dioxane, tetrahydrofuran, glycol dimethyl ether or diethylene glycol dimethyl ether, or other solvents such as dimethylformamide (DMF), dimethyl sulfoxide (DMSO), N,N'-dimethylpropyleneurea (DMPU), N-methylpyrrolidone (NMP), pyridine, acetonitrile or else water. It is also possible to use mixtures of the solvents mentioned. Preference is given to DMF and pyridine.

Suitable catalysts for the reduction (X)→(III) are, for example, palladium on activated carbon, platinum on carbon, palladium hydroxide or Raney nickel.

The reduction (X)→(III) can alternatively be carried out using a metal or metal salt, for example iron, zinc or tin(II) chloride in a suitable acid, for example hydrogen chloride/hydrochloric acid, sulfuric acid, phosphoric acid or acetic acid, in a temperature range of +20° C. to +140° C.

The preparation process described can be illustrated by way of example by the following synthesis scheme (Scheme 3):

Scheme 3:

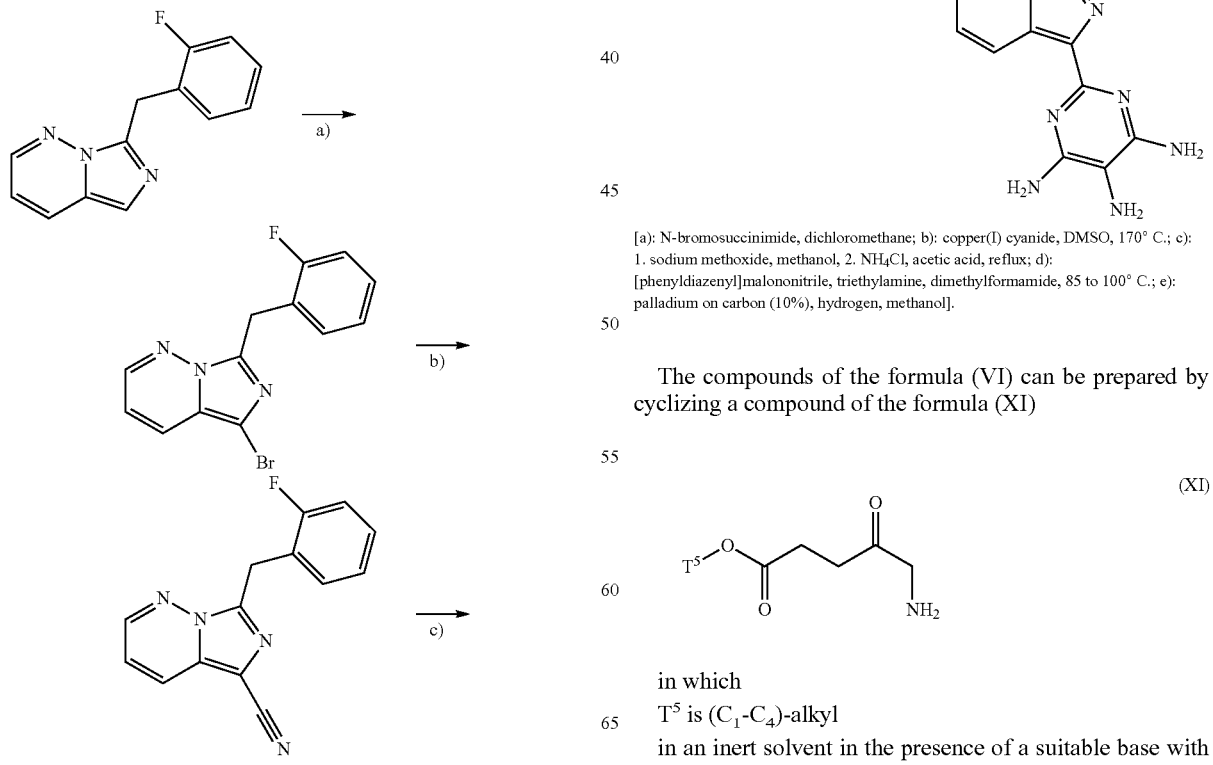

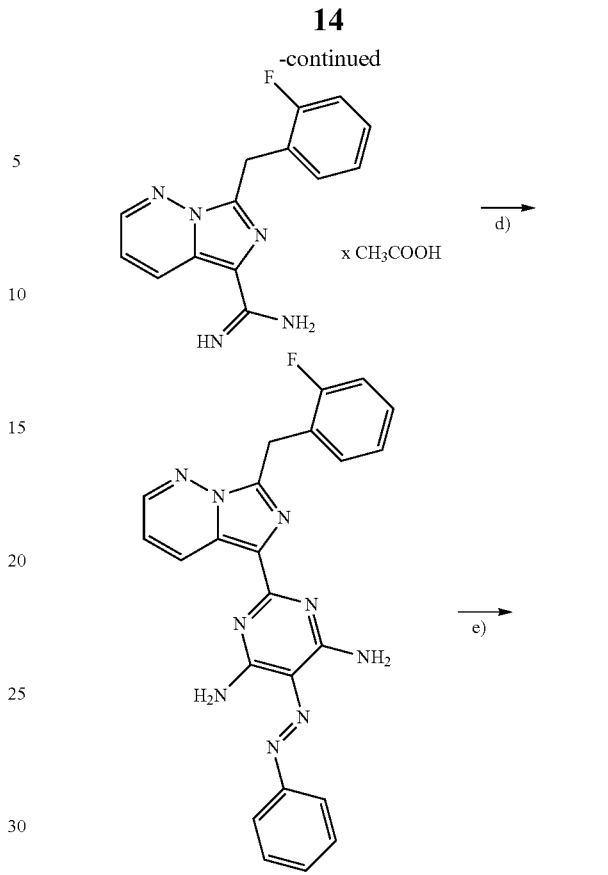

[a]: N-bromosuccinimide, dichloromethane; b): copper(I) cyanide, DMSO, 170° C.; c): 1. sodium methoxide, methanol, 2. NH₄Cl, acetic acid, reflux; d): [phenyldiazenyl]malononitrile, triethylamine, dimethylformamide, 85 to 100° C.; e): palladium on carbon (10%), hydrogen, methanol].

The compounds of the formula (VI) can be prepared by cyclizing a compound of the formula (XI)

(XI)

in which $T^5$ is $(C_1\text{-}C_4)$-alkyl in an inert solvent in the presence of a suitable base with hydrazine hydrate to give a compound of the formula (XII)

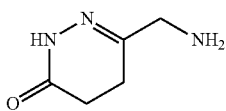

then reacting the latter in an inert solvent, in the presence of a suitable base, with a compound of the formula (XIII)

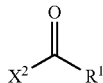

in which R¹ has the meaning given above and
X² is halogen, in particular chlorine or bromine,
to give a compound of the formula (XIV)

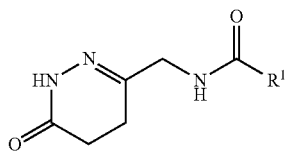

in which R¹ has the meaning given above,
then oxidizing the latter to a compound of the formula (XV)

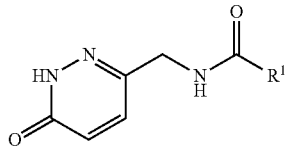

in which R¹ has the meaning given above,
furthermore cyclizing the latter in the absence of a solvent or in an inert solvent with phosphorus oxychloride to give a compound of the formula (XVI)

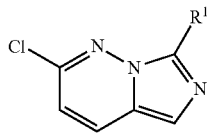

in which R¹ has the meaning given above,
and finally hydrogenating in an inert solvent in the presence of a suitable base.

The compounds of the formulae (XI) and (XII) are commercially available, known from the literature or can be prepared in analogy to literature processes.

Inert solvents for the process step (XI)→(XII) are alcohols such as methanol, ethanol, n-propanol, isopropanol, n-butanol or tert-butanol, ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), N-methylpyrrolidone (NMP), pyridine, acetonitrile or else water. It is also possible to use mixtures of the solvents mentioned. Preference is given to ethanol.

Suitable bases for the process step (XI)→(XII) are alkali metal hydroxides such as, for example, lithium hydroxide, sodium hydroxide or potassium hydroxide, alkali metal carbonates such as lithium carbonate, sodium carbonate, potassium carbonate or cesium carbonate, alkali metal bicarbonates such as sodium bicarbonate or potassium bicarbonate, alkali metal alkoxides such as sodium methoxide or potassium methoxide, sodium ethoxide or potassium ethoxide or potassium tert-butoxide, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to triethylamine.

The reaction (XI)→(XII) is generally carried out in a temperature range of from +20° C. to +150° C., preferably at from +80° C. to +120° C., optionally in a microwave. The reaction can be carried out at atmospheric, elevated or reduced pressure (for example from 0.5 to 5 bar). The reaction is generally carried out at atmospheric pressure.

Inert solvents for the process step (XII)+(XIII)→(XIV) are ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, halogenated hydrocarbons such as dichloromethane, trichloromethane, carbon tetrachloride, trichloroethylene or chlorobenzene, or other solvents such as dimethylformamide (DMF), dimethyl sulfoxide (DMSO), N,N'-dimethylpropyleneurea (DMPU), N-methylpyrrolidone (NMP), pyridine or acetonitrile. It is also possible to use mixtures of the solvents mentioned. Preference is given to acetonitrile.

Suitable bases for the process step (XII)+(XIII)→(XIV) are alkali metal carbonates such as lithium carbonate, sodium carbonate, potassium carbonate or cesium carbonate, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to triethylamine The reaction (XII)+(XIII)→(XIV) is generally carried out in a temperature range from −20° C. to +40° C., preferably at from 0° C. to +20° C. The reaction can be carried out at atmospheric, elevated or reduced pressure (for example from 0.5 to 5 bar). The reaction is generally carried out at atmospheric pressure.

The oxidation (XIV)→(XV) is preferably carried out in an organic acid such as, for example, formic acid or acetic acid, in the presence of elemental bromine at a temperature of from +40° C. to +100° C.

The cyclization (XV)→(XVI) is carried out in the absence of a solvent or in a solvent which is inert under all reaction conditions. Suitable solvents are, for example, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), N-methylpyrrolidone (NMP), pyridine, sulfolane or acetonitrile. Preference is given to using sulfolane.

The cyclization (XV)→(XVI) is generally carried out in a temperature range from +50° C. to +140° C., preferably at from +80° C. to +120° C. The reaction can be carried out at atmospheric, elevated or reduced pressure (for example from 0.5 to 5 bar). The reaction is generally carried out at atmospheric pressure.

The process step (XVI)→(VI) is carried out in a solvent which is inert under the reaction conditions, for example alcohols such as methanol, ethanol, n-propanol, isopropanol, n-butanol or tert-butanol, ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, or other solvents such as ethyl acetate, dimethylformamide (DMF), dimethyl sulfoxide (DMSO), N,N'-dimethylpropyleneurea (DMPU), N-methylpyrrolidone (NMP), pyridine, sulfolane or acetonitrile. Preference is given to ethyl acetate.

Suitable bases for the process step (XVI)→(VI) are organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to triethylamine.

The cyclization (XVI)→(VI) is generally carried out in a temperature range from 0° C. to +60° C., preferably at from +10° C. to +30° C.

The scheme below (Scheme 4) shows, in an exemplary manner, the preparation process described above:

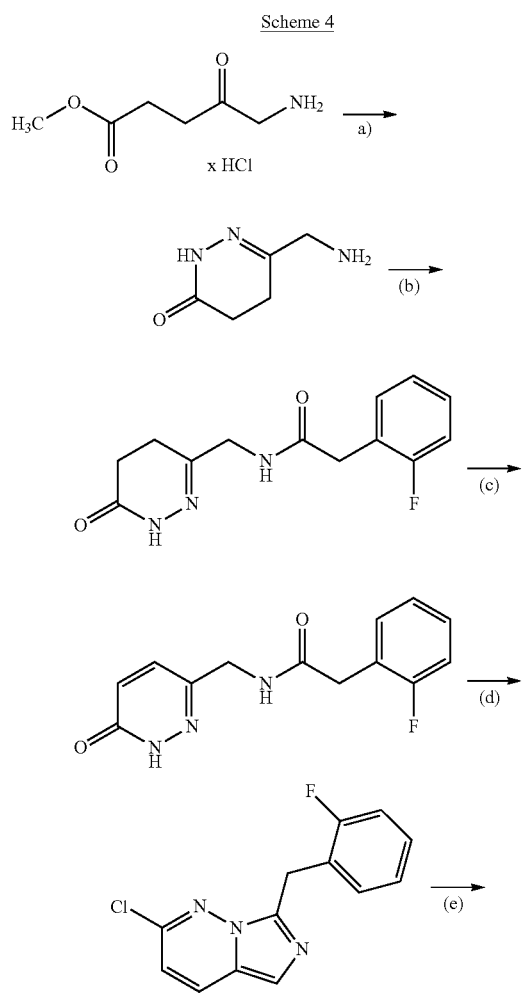

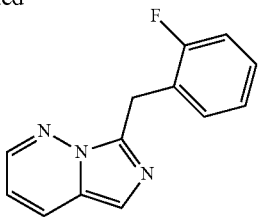

[a): hydrazine hydrate, triethylamine, ethanol, reflux; b) (2-fluorophenyl)acetyl chloride, triethylamine, acetonitrile; c): bromine, acetic acid, 50° C.; d): phosphorus oxychloride, sulfolane, 100° C.; e) palladium on carbon (5%), triethylamine, hydrogen, ethyl acetate].

The compounds according to the invention act as potent stimulators of soluble guanylate cyclase, have useful pharmacological and are therefore suitable for treatment and/or prophylaxis of disorders in humans and animals.

The compounds according to the invention cause vasorelaxation and inhibition of platelet aggregation, and lead to a decrease in blood pressure and to a rise in coronary blood flow. These effects are mediated by direct stimulation of soluble guanylate cyclase and an intracellular rise in cGMP. In addition, the compounds according to the invention enhance the action of substances which increase the cGMP level, for example EDRF (endothelium-derived relaxing factor), NO donors, protoporphyrin IX, arachidonic acid or phenylhydrazine derivatives.

The compounds according to the invention are suitable for treatment and/or prophylaxis of cardiovascular, pulmonary, thromboembolic and fibrotic disorders.

The compounds according to the invention can therefore be used in medicaments for treatment and/or prophylaxis of cardiovascular disorders, for example hypertension, acute and chronic heart failure, coronary heart disease, stable and unstable angina pectoris, peripheral and cardiovascular disorders, arrhythmias, atrial and ventricular arrhythmias and impaired conduction, for example atrioventricular grade I-III blocks (AB block I-III), supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, Sick-Sinus syndrome, syncopes, AV-nodal re-entry tachycardia, Wolff-Parkinson-White syndrome, acute coronary syndrome (ACS), autoimmune cardiac disorders (pericarditis, endocarditis, valvolitis, aortitis, cardiomyopathies), shock such as cardiogenic shock, septic shock and anaphylactic shock, aneurysms, boxer cardiomyopathy (premature ventricular contraction (PVC)), for treatment and/or prophylaxis of thromboembolic disorders and ischemias such as myocardial ischemia, myocardial infarction, stroke, cardiac hypertrophy, transient and ischemic attacks, preeclampsia, inflammatory cardiovascular disorders, spasms of the coronary arteries and peripheral arteries, edema formation, for example pulmonary edema, cerebral edema, renal edema or edema caused by heart failure, impaired peripheral perfusion, reperfusion damage, arterial and venous thromboses, microalbuminuria, myocardial insufficiency, endothelial dysfunction, for prevention of restenoses, such as after thrombolysis treatments, percutaneous transluminal angioplasties (PTA), percutaneous transluminal coronary angioplasties (PTCA), heart transplants and bypass operations, and micro- and macrovascular damage (vasculitis), elevated levels of fibrinogen and of low-density LDL, and elevated concentrations of plasminogen activator inhibitor 1 (PAI-1), and for treatment and/or prophylaxis of erectile dysfunction and female sexual dysfunction.

In the context of the present invention, the term "heart failure" also encompasses both acute and chronic forms of heart failure, and also more specific or related types of disease, such as acute decompensated heart failure, right heart failure, left heart failure, global failure, ischemic cardiomyopathy, dilated cardiomyopathy, hypertrophic cardiomyopathy, idiopathic cardiomyopathy, congenital heart defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, diastolic heart failure and systolic heart failure, and acute phases of worsening of existing chronic heart failure (worsening heart failure).

In addition, the compounds according to the invention can also be used for the treatment and/or prophylaxis of arteriosclerosis, impaired lipid metabolism, hypolipoproteinemias, dyslipidemias, hypertriglyceridemias, hyperlipidemias, hypercholesterolemias, abetalipoproteinemias, sitosterolemia, xanthomatosis, Tangier disease, adiposity, obesity and of combined hyperlipidemias and metabolic syndrome.

Moreover, the compounds according to the invention can be used for treatment and/or prophylaxis of primary and secondary Raynaud's phenomenon, of microcirculation disorders, claudication, peripheral and autonomic neuropathies, diabetic microangiopathies, diabetic retinopathy, diabetic ulcers at the extremities, gangrene, CREST syndrome, erythematosis, onychomycosis, rheumatic disorders, and for promotion of wound healing.

The compounds according to the invention are furthermore suitable for treating urological disorders such as, for example, benign prostate syndrome (BPS), benign prostate hyperplasia (BPH), benign prostate enlargement (BPE), bladder outlet obstruction (BOO), lower urinary tract syndromes (LUTS, including Feline Urological Syndrome (FUS)), disorders of the urogenital system including neurogenic over-active bladder (OAB) and (IC), incontinence (UI) such as, for example, mixed urinary incontinence, urge urinary incontinence, stress urinary incontinence or overflow urinary incontinence (MUI, UUI, SUI, OUI), pelvic pain, benign and malignant disorders of the organs of the male and femal urogenital system.

The compounds according to the invention are furthermore suitable for the treatment and/or prophylaxis of kidney disorders, in particular of acute and chronic renal insufficiency and acute and chronic renal failure In the context of the present invention, the term "renal insufficiency" encompasses both acute and chronic manifestations of renal insufficiency, and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immunocomplex-induced kidney disorders, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome which can be characterized diagnostically, for example, by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphatemia and/or need for dialysis. The present invention also encompasses the use of the compounds according to the invention for treatment and/or prophylaxis of sequelae of renal insufficiency, for example pulmonary edema, heart failure, uremia, anemia, electrolyte disturbances (for example hypercalcemia, hyponatremia) and disturbances in bone and carbohydrate metabolism.

Furthermore, the compounds according to the invention are also suitable for treatment and/or prophylaxis of asthmatic disorders, pulmonary arterial hypertension (PAH) and other forms of pulmonary hypertension (PH) including pulmonary hypertension associated with left heart disease, HIV, sickle cell anemia, thromboembolisms (CTEPH), sarcoidosis, COPD or pulmonary fibrosis, or chronic-obstructive pulmonary disease (COPD), acute respiratory distress syndrome (ARDS), acute lung injury (ALI), alpha-1 antitrypsin deficiency (AATD), pulmonary fibrosis, pulmonary emphysema (for example pulmonary emphysema induced by cigarette smoke) and cystic fibrosis (CF).

The compounds described in the present invention are also active compounds for control of central nervous system disorders characterized by disturbances of the NO/cGMP system. More particularly, they are suitable for improving perception, concentration, learning or memory after cognitive impairments such as those occurring particularly in the event of situations/diseases/syndromes such as mild cognitive impairment, age-associated learning and memory impairments, age-associated memory losses, vascular dementia, craniocerebral trauma, stroke, dementia occurring after strokes (post-stroke dementia), post-traumatic craniocerebral trauma, general concentration impairments, concentration impairments in children having learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelination, multiple sclerosis, thalamic degeneration, Creutzfeld-Jacob dementia, HIV dementia, schizophrenia with dementia or Korsakoff's psychosis. They are also suitable for treatment and/or prophylaxis of central nervous system disorders such as states of anxiety, tension and depression, CNS-related sexual dysfunction and disrupted sleep, and for control of pathological disturbances of the intake of food, stimulants and addictive substances.

Furthermore, the compounds according to the invention are also suitable for regulating cerebral blood flow and are thus effective agents for control of migraine. They are also suitable for prophylaxis and control of sequelae of cerebral infarct (cerebral apoplexy) such as stroke, cerebral ischemia and craniocerebral trauma. The compounds according to the invention can likewise be employed for controlling states of pain and tinnitus.

In addition, the compounds according to the invention have antiinflammatory action and can therefore be used as antiinflammatory agents for the treatment and/or prophylaxis of sepsis (SIRS), multiple organ failure (MODS, MOF), inflammatory disorders of the kidney, chronic intestinal inflammations (IBD, Crohn's disease, UC), pancreatitis, peritonitis, rheumatoid disorders, inflammatory skin diseases and inflammatory eye diseases.

Furthermore, the compounds according to the invention can also be used for the treatment and/or prophylaxis of autoimmune diseases.

The compounds according to the invention are furthermore suitable for the treatment and/or prophylaxis of fibrotic disorders of the internal organs such as, for example, the lung, the heart, the kidney, the bone marrow and in particular the liver, and also dermatological fibroses and fibrotic eye disorders. In the context of the present inventions, the term "fibrotic disorders" encompasses especially the following terms: hepatic fibrosis, hepatic cirrhosis, pulmonary fibrosis, endomyocardial fibrosis, nephropathy, glomerulonephritis, interstitial renal fibrosis, fibrotic damage resulting from diabetes, myelofibrosis and similar fibrotic disorders, scleroderma, morphea, keloids, hypertrophic scarring (including after surgical interventions), naevi, diabetic retinopathy, proliferative vitreoretinopathy and disorders of the connective tissue (for example sarcoidosis).

Furthermore, the compounds according to the invention are suitable for control of postoperative scarring, for example resulting from glaucoma operations.

The compounds according to the invention can also be used cosmetically for ageing and keratinized skin.

Moreover, the compounds according to the invention are suitable for the treatment and/or prophylaxis of hepatitis, neoplasms, osteoporosis, glaucoma and gastroparesis.

The present invention further provides for the use of the compounds according to the invention for the treatment and/or prophylaxis of disorders, in particular the disorders mentioned above.

The present invention further provides for the use of the compounds according to the invention for treatment and/or prophylaxis of heart failure, angina pectoris, hypertension, pulmonary hypertension, ischemia, vascular disorders, renal insufficiency, thromboembolic disorders, fibrotic disorders and arteriosclerosis.

The present invention further provides the compounds according to the invention for use in a method for treatment and/or prophylaxis of heart failure, angina pectoris, hypertension, pulmonary hypertension, ischemia, vascular disorders, kidney failure, thromboembolic disorders, fibrotic disorders and arteriosclerosis.

The present invention further provides for the use of the compounds according to the invention for production of a medicament for treatment and/or prophylaxis of disorders, especially of the aforementioned disorders.

The present invention further provides for the use of the compounds according to the invention for production of a medicament for treatment and/or prophylaxis of heart failure, angina pectoris, hypertension, pulmonary hypertension, ischemia, vascular disorders, kidney failure, thromboembolic disorders, fibrotic disorders and arteriosclerosis.

The present invention further provides a method for treatment and/or prophylaxis of disorders, in particular the disorders mentioned above, using an effective amount of at least one of the compounds according to the invention.

The present invention further provides a method for treatment and/or prophylaxis of heart failure, angina pectoris, hypertension, pulmonary hypertension, ischemia, vascular disorders, kidney failure, thromboembolic disorders, fibrotic disorders and arteriosclerosis using an effective amount of at least one of the compounds according to the invention.

The compounds according to the invention can be employed alone or, if required, in combination with other active compounds. The present invention further provides medicaments comprising at least one of the compounds according to the invention and one or more further active compounds, especially for the treatment and/or prophylaxis of the aforementioned disorders. Preferred examples of suitable active compound combinations include:

organic nitrates and NO donors, for example sodium nitroprusside, nitroglycerine, isosorbide mononitrate, isosorbide dinitrate, molsidomine or SIN1, and inhaled NO;

compounds which inhibit the breakdown of cyclic guanosine monophosphate (cGMP), for example inhibitors of phosphodiesterases (PDE) 1, 2 and/or 5, especially PDE 5 inhibitors such as sildenafil, vardenafil and tadalafil;

antithrombotic agents, by way of example and with preference from the group of the platelet aggregation inhibitors, the anticoagulants or the profibrinolytic substances;

hypotensive active compounds, by way of example and with preference from the group of the calcium antagonists, angiotensin AII antagonists, ACE inhibitors, endothelin antagonists, renin inhibitors, alpha-receptor blockers, beta-receptor blockers, mineralocorticoid receptor antagonists, and the diuretics; and/or active compounds which modify lipid metabolism, by way of example and with preference from the group of thyroid receptor agonists, cholesterol synthesis inhibitors such as, by way of example and with preference, HMG-CoA reductase inhibitors or squalene synthesis inhibitors, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein (a) antagonists.

Antithrombotic agents are preferably understood to mean compounds from the group of the platelet aggregation inhibitors, the anticoagulants or the profibrinolytic substances.

In a preferred embodiment of the invention, the compounds according to the invention are administered in combination with a platelet aggregation inhibitor such as, by way of example and with preference aspirin, clopidogrel, ticlopidin or dipyridamol.

In a preferred embodiment of the invention, the compounds according to the invention are administered in combination with a thrombin inhibitor, by way of example and with preference ximelagatran, dabigatran, melagatran, bivalirudin or clexane.

In a preferred embodiment of the invention, the compounds according to the invention are administered in combination with a GPIIb/IIIa antagonist such as, by way of example and with preference tirofiban or abciximab.

In a preferred embodiment of the invention, the compounds according to the invention are administered in combination with a factor Xa inhibitor, by way of example and with preference rivaroxaban (BAY 59-7939), DU176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or with a low molecular weight (LMW) heparin derivative.

In a preferred embodiment of the invention, the compounds according to the invention are administered in combination with a vitamin K antagonist, by way of example and with preference coumarin.

Hypotensive agents are preferably understood to mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, and the diuretics.

In a preferred embodiment of the invention, the compounds according to the invention are administered in combination with a calcium antagonist, by way of example and with preference nifedipine, amlodipine, verapamil or diltiazem.

In a preferred embodiment of the invention, the compounds according to the invention are administered in combination with an alpha-1-receptor blocker, by way of example and with preference prazosin.

In a preferred embodiment of the invention, the compounds according to the invention are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist, by way of example and with preference losartan, candesartan, valsartan, telmisartan or embusartan.

In a preferred embodiment of the invention, the compounds according to the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds according to the invention are administered in combination with an endothelin antagonist, by way of example and with preference bosentan, darusentan, ambrisentan or sitaxsentan.

In a preferred embodiment of the invention, the compounds according to the invention are administered in combination with a renin inhibitor, by way of example and with preference aliskiren, SPP600 or SPP800.

In a preferred embodiment of the invention, the compounds according to the invention are administered in combination with a mineralocorticoid receptor antagonist, by way of example and with preference spironolactone or eplerenone.

In a preferred embodiment of the invention, the compounds according to the invention are administered in combination with a loop diuretic, for example furosemide, torasemide, bumetanide and piretanide, with potassium-sparing diuretics, for example amiloride and triamterene, with aldosterone antagonists, for example spironolactone, potassium canrenoate and eplerenone, and also thiazide diuretics, for example hydrochlorothiazide, chlorthalidone, xipamide and indapamide.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and the lipoprotein (a) antagonists.

In a preferred embodiment of the invention, the compounds according to the invention are administered in combination with a CETP inhibitor, by way of example and with preference dalcetrapib, BAY 60-5521, anacetrapib or CETP vaccine (CETi-1).

In a preferred embodiment of the invention, the compounds according to the invention are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, by way of example and with preference BMS188494 or TAK475.

In a preferred embodiment of the invention, the compounds according to the invention are administered in combination with an ACAT inhibitor, by way of example and with preference avasimibe, melinamide, pactimibe, eflucimibe or SMP797.

In a preferred embodiment of the invention, the compounds according to the invention are administered in combination with an MTP inhibitor, by way of example and with preference implitapide, BMS201038, R103757 or JTT130.

In a preferred embodiment of the invention, the compounds according to the invention are administered in combination with a PPAR-gamma agonist, by way of example and with preference pioglitazone or rosiglitazone.

In a preferred embodiment of the invention, the compounds according to the invention are administered in combination with a PPAR-delta agonist, by way of example and with preference GW 501516 or BAY 685042.

In a preferred embodiment of the invention, the compounds according to the invention are administered in combination with a cholesterol absorption inhibitor, by way of example and with preference ezetimibe, tiqueside or pamaqueside.

In a preferred embodiment of the invention, the compounds according to the invention are administered in combination with a lipase inhibitor, by way of example and with preference orlistat.

In a preferred embodiment of the invention, the compounds according to the invention are administered in combination with a polymeric bile acid adsorbent, by way of example and with preference cholestyramine, colestipol, colesolvam, CholestaGel or colestimide.

In a preferred embodiment of the invention, the compounds according to the invention are administered in combination with a bile acid reabsorption inhibitor, by way of example and with preference ASBT (=IBAT) inhibitors, for example AZD7806, S8921, AK105, BARI1741, SC435 or SC635.

In a preferred embodiment of the invention, the compounds according to the invention are administered in combination with a lipoprotein (a) antagonist, by way of example and with preference gemcabene calcium (CI1027) or nicotinic acid.

The present invention further provides medicaments which comprise at least one compound according to the invention, typically together with one or more inert, nontoxic, pharmaceutically suitable auxiliaries, and for the use thereof for the aforementioned purposes.

The compounds according to the invention may act systemically and/or locally. For this purpose, they can be administered in a suitable manner, for example by the oral, parenteral, pulmonal, nasal, sublingual, lingual, buccal, rectal, dermal, transdermal, conjunctival, otic route, or as an implant or stent.

The compounds according to the invention can be administered in administration forms suitable for these administration routes.

Suitable administration forms for oral administration are those which work according to the prior art, which release the compounds according to the invention rapidly and/or in a modified manner and which contain the compounds according to the invention in crystalline and/or amorphized and/or dissolved form, for example tablets (uncoated or coated tablets, for example with gastric juice-resistant or retarded-dissolution or insoluble coatings which control the release of the compound according to the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can be accomplished with avoidance of an absorption step (for example by an intravenous, intraarterial, intracardiac, intraspinal or intralumbar route) or with inclusion of an absorption (for example by an intramuscular, subcutaneous, intracutaneous, percutaneous or intraperitoneal route). Administration forms suitable for parenteral administration include preparations for injection and infusion in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Preference is given to oral or parenteral administration, especially oral administration.

The compounds according to the invention can be converted to the administration forms mentioned. This can be accomplished in a manner known per se by mixing with inert nontoxic pharmaceutically suitable auxiliaries. These auxiliaries include carriers (for example microcrystalline cellulose, lactose, mannitol), solvents (e.g. liquid polyethylene glycols), emulsifiers and dispersing or wetting agents (for example sodium dodecylsulfate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavor and/or odor correctors.

In general, it has been found to be advantageous in the case of parenteral administration to administer amounts of from about 0.001 to 1 mg/kg, preferably about 0.01 to 0.5 mg/kg of body weight to achieve effective results. In the case of oral administration the dosage is about 0.01 to 100 mg/kg, preferably about 0.01 to 20 mg/kg and most preferably 0.1 to 10 mg/kg of body weight.

It may nevertheless be necessary in some cases to deviate from the stated amounts, specifically as a function of the body weight, route of administration, individual response to the active ingredient, nature of the preparation and time or interval over which administration takes place. Thus, in some cases less than the abovementioned minimum amount may be sufficient, while in other cases the upper limit mentioned must be exceeded. In the case of administration of relatively large amounts, it may be advisable to divide these into several individual doses over the course of the day.

The working examples which follow illustrate the invention. The invention is not restricted to the examples.

The percentages in the tests and examples which follow are, unless stated otherwise, percentages by weight; parts are parts by weight. Solvent ratios, dilution ratios and concentration figures for liquid/liquid solutions are each based on volume.

A. EXAMPLES

Abbreviations and Acronyms aq. aqueous solution
calc. calculated
DCI direct chemical ionization (in MS)
DMF dimethylformamide
DMSO dimethyl sulfoxide
eq. equivalent(s)
ESI electrospray ionization (in MS)
Et ethyl
h hour(s)
HPLC high-pressure, high-performance liquid chromatography
HRMS high-resolution mass spectrometry
conc. concentrated
LC/MS liquid chromatography-coupled mass spectrometry
Me methyl
min minute(s)
MS mass spectrometry
NMR nuclear magnetic resonance spectrometry
Ph phenyl
RT room temperature
$R_t$ retention time (in HPLC)
THF tetrahydrofuran
UV ultraviolet spectrometry
v/v ratio by volume (of a solution)

LC/MS Methods

Method 1 (LC-MS):
Instrument: Micromass Quattro Micro MS with HPLC Agilent Series 1100; column: Thermo Hypersil GOLD 3µ, 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.

Method 2 (LC-MS):
Instrument: Waters ACQUITY SQD UPLC System; column: Waters Acquity UPLC HSS T3 1.8µ 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 210-400 nm.

Starting Materials and Intermediates

Example 1A 2-(2-Fluorophenyl)-N-[(6-oxo-1,4,5,6-tetrahydropyridazin-3-yl)methyl]acetamide

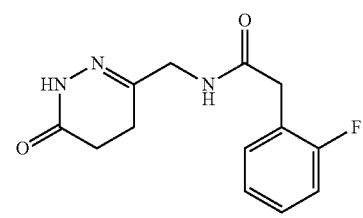 [SMILES: O=C(Cc1ccccc1F)NCC1=NNC(=O)CC1]

200.00 g (1.101 mol) of methyl 5-amino-4-oxopentanoate hydrochloride were initially charged in ethanol (3500 ml), 64.28 ml (1.321 mol) of hydrazine hydrate were added and the mixture was then heated at reflux for 45 min. After cooling, triethylamine (152 ml) was added and the mixture was evaporated to dryness. Water (500 ml) was added to the residue, and the mixture was concentrated. Ethanol (500 ml) was then added, the mixture was concentrated, and then toluene (500 ml) was added twice, followed in each case by evaporation to dryness. The residue (140 g) was dissolved in acetonitrile (500 ml) and, at 0° C., added dropwise to a solution of 307.85 g (1.784 mol) of (2-fluorophenyl)acetyl chloride (preparation: Journal of Organic Chemistry; 22; 1957; 879) and 304.86 ml (2.202 mol) of triethylamine in acetonitrile (1500 ml) and molecular sieve. The mixture was stirred at 20° C. for 3 days. The mixture was then filtered and the precipitate was washed with tert-butyl methyl ether and then dried. This gave 458 g of the target compound (90% of theory).

LC-MS (method 2): $R_t$=0.57 min; MS (EIpos): m/z=264 [M+H]$^+$.

Example 2A 2-(2-Fluorophenyl)-N-[(6-oxo-1,6-dihydropyridazin-3-yl)methyl]acetamide

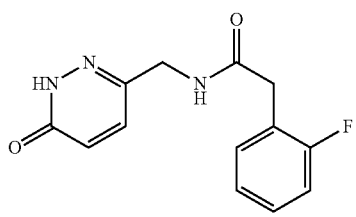 [SMILES: O=C(Cc1ccccc1F)NCc1ccc(=O)[nH]n1]

458 g (1.740 mol) of the compound obtained in Example 1A were initially charged in acetic acid (2250 ml), and the mixture was warmed to 50° C. At this temperature, 98.16 ml (1.914 mol) of bromine were added dropwise with vigorous stirring, and stirring was then continued at 50° C. for 3 h. After cooling, the mixture was concentrated to dryness. The residue was stirred with saturated aqueous sodium bicarbonate solution (4800 ml). The mixture was then filtered and the precipitate was washed with a little water. The filtrate was extracted twice with ethyl acetate. The organic phases were combined, dried and concentrated. This gave 117 g of the target compound (25% of theory).

LC-MS (method 2): $R_t$=0.56 min; MS (EIpos): m/z=262 [M+H]$^+$.

$^1$H NMR (400 MHz, DMSO-d$_6$): δ [ppm]=3.54 (s, 2H), 4.16 (d, 2H), 6.86 (d, 1H), 7.12-7.16 (m, 2H), 7.27-7.35 (m, 3H), 8.62 (t, 1H), 12.88 (s, 1H).

Example 3A

2-Chloro-7-(2-fluorobenzyl)imidazo[1,5-b]pyridazine

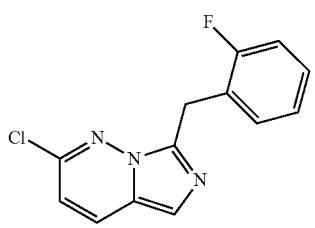 [SMILES: Fc1ccccc1Cc1ncc2ccc(Cl)nn12]

65.00 g (248.79 mmol) of the compound obtained in Example 2A were initially charged in sulfolane (780 ml), 185.52 ml (1.990 mol) of phosphorus oxychloride were added and the mixture was then stirred at 100° C. for 3 h. Excess phosphorus oxychloride was then distilled off under high vacuum, and the residue was taken up in ethyl acetate and added to a saturated aqueous sodium bicarbonate solution. The mixture was diluted with water and then extracted with ethyl acetate. The organic phases were combined, washed with water, dried and concentrated. The residue was purified by chromatography on silica gel (mobile phase: dichloromethane/methanol 20:1→5:1 (v/v)), then washed once more with water and purified once more by chromatography on silica gel (mobile phase:dichloromethane/methanol 100:1 v/v). This gave 23.6 g of the target compound (36% of theory).

LC-MS (method 2): $R_t$=1.00 min; MS (EIpos): m/z=262 [M+H]$^+$.

$^1$H NMR (400 MHz, DMSO-d$_6$): δ [ppm]=4.40 (s, 2H), 6.84 (d, 1H), 7.10-7.33 (m, 4H), 7.55 (s, 1H), 8.19 (d, 1H).

Example 4A 7-(2-Fluorobenzyl)imidazo[1,5-b]pyridazine

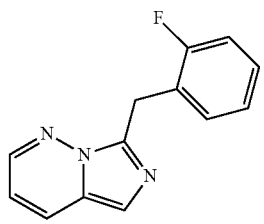 [SMILES: Fc1ccccc1Cc1ncc2cccnn12]

2.004 g of palladium on carbon (5%) were initially charged under argon, and 20.04 g (76.58 mmol) of the compound obtained in Example 3A in ethyl acetate (750 ml) were then added. 21.348 ml (153.159 mmol) of triethylamine were then added, and the reaction mixture was hydrogenated at standard hydrogen pressure and 20° C. for 16 hours. The same amount of catalyst as indicated above was then added, and the reaction mixture was hydrogenated at standard hydrogen pressure and 20° C. for another night. The mixture was then filtered through Celite, the filter cake was washed with ethanol and the filtrate was concentrated and dried under high vacuum. This gave 22.79 g of the target compound (about 100% of theory, contaminated with triethylamine).

LC-MS (method 2): $R_t$=0.77 min; MS (EIpos): m/z=228 [M+H]$^+$.

$^1$H NMR (400 MHz, DMSO-d$_6$): δ [ppm]=4.44 (s, 2H), 6.70 (dd, 1H), 7.08-7.31 (m, 4H), 7.45 (s, 1H), 8.09 (dd, 1H), 8.28 (dd, 1H).

Example 5A

5-Bromo-7-(2-fluorobenzyl)imidazo[1,5-b]pyridazine 22.46 g (98.837 mmol) of the compound obtained in Example 4A were initially charged in dichloromethane (400 ml), and 17.591 g (98.837 mmol) of N-bromosuccinimide were then added. The mixture was then stirred at 20° C. for 10 min. Water was then added, the phases were separated and the organic phase was washed with water. The aqueous phase was extracted twice with dichloromethane and the combined organic phases were washed with saturated aqueous sodium chloride solution, dried over sodium sulfate, filtered and concentrated. This gave 22.78 g of the target compound (75% of theory).

LC-MS (method 2): $R_t$=1.05 min; MS (EIpos): m/z=306, 308 [M+H, bromine pattern]$^+$.

$^1$H NMR (400 MHz, DMSO-d$_6$): δ [ppm]=4.45 (s, 2H), 6.81 (dd, 1H), 7.12-7.34 (m, 4H), 7.94 (dd, 1H), 8.28 (dd, 1H).

Example 6A 7-(2-Fluorobenzyl)imidazo[1,5-b]pyridazine-5-carbonitrile

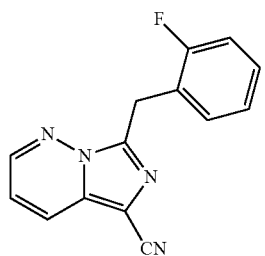 [SMILES: N#Cc1nc(Cc2ccccc2F)n2ncccc12]

1.00 g (3.266 mmol) of the compound obtained in Example 5A were initially charged in dry DMSO (25 ml), 1.170 g (13.066 mmol) of copper(I) cyanide were then added and, with stirring, the mixture was heated to 170° C. for 3.5 h. The mixture was filtered through Celite, and the filter cake was washed with ethyl acetate and tetrahydrofuran. The filtrate was then extracted four times with a mixture of saturated aqueous ammonium chloride solution/aqueous ammonia (33%) (3:1, v/v) and washed once with saturated aqueous sodium chloride solution. The phases were separated and the organic phase was dried with sodium sulfate, filtered and concentrated. The residue was treated with ethanol in an ultrasonic bath, and water was then added. The precipitate formed was filtered off, washed with ethanol and then dried under high vacuum. This gave 586 mg of the target compound (71% of theory).

LC-MS (method 2): $R_t$=0.95 min; MS (EIpos): m/z=253 [M+H]$^+$.

$^1$H NMR (400 MHz, DMSO-d$_6$): δ [ppm]=4.49 (s, 2H), 7.13-7.35 (m, 5H), 8.40 (d, 1H), 8.61 (d, 1H).

Example 7A 7-(2-Fluorobenzyl)imidazo[1,5-b]pyridazine-5-carboximidamide acetate

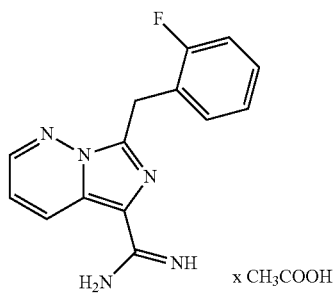 [SMILES: N=C(N)c1nc(Cc2ccccc2F)n2ncccc12]

584 mg (2.315 mmol) of the compound prepared in Example 6A were added to 125 mg (2.315 mmol) of sodium methoxide in methanol (10 ml), and the mixture was stirred at 20° C. for 16 hours. 148 mg (2.778 mmol) of ammonium chloride and acetic acid (0.517 ml) were then added, and the mixture was heated at reflux for 8 h. The mixture was then concentrated to dryness, the residue was taken up in water and ethyl acetate and 1 N aqueous sodium hydroxide solution was added. The phases were separated and the aqueous phase was extracted twice with ethyl acetate. The combined organic phases were dried over sodium sulfate, filtered, concentrated and then dried under high vacuum. This gave 543 mg of the target compound (71% of theory).

LC-MS (method 2): $R_t$=0.63 min; MS (EIpos): m/z=270 [M+H]$^+$.

Example 8A

2-[7-(2-Fluorobenzyl)imidazo[1,5-b]pyridazin-5-yl]-5-[(E)-phenyldiazenyl]pyrimidine-4,6-diamine

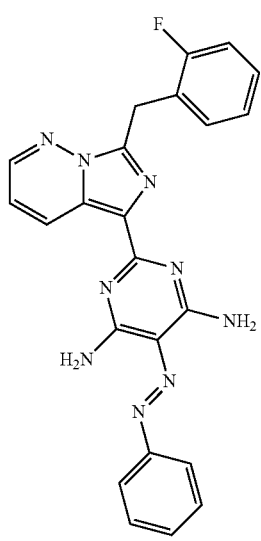 [SMILES: Nc1nc(-c2nc(Cc3ccccc3F)n3ncccc23)nc(N)c1/N=N/c1ccccc1]

Step a) [Phenyldiazenyl]malononitrile

Conc. hydrochloric acid (17.84 ml) and then a solution of 7.409 g (107.377 mmol) of sodium nitrite in water (18 ml)

were added dropwise to 10.00 g (107.377 mmol) of aniline and ice (32 g) in an ice bath between 0° C. and 5° C., and the mixture was stirred at 0° C. for 30 min. At 0° C., a solution of 11.099 g (135.296 mmol) of sodium acetate in water (75 ml) was then added, and a solution of 7.049 g (107.377 mmol) of malononitrile in ethanol (6.5 ml) was subsequently added dropwise with stirring. After 2 h at 0° C., the resulting precipitate was filtered off with suction and washed with water (107 ml).

Step b) 2-[7-(2-Fluorobenzyl)imidazo[1,5-b]pyridazin-5-yl]-5-[(E)-phenyldiazenyl]pyrimidine-4,6-diamine 2.85 g (16.745 mmol) of [phenyldiazenyl]malononitrile (step a)) were dissolved in DMF (0.5 ml) and, at 85° C. exactly, added dropwise to a solution of 4.266 g (13.954 mmol) of Example 7A in DMF (0.5 ml) and triethylamine (2.139 ml). The mixture was then stirred at 100° C. for 3 h, and another 2.85 g (16.745 mmol) of [phenyldiazenyl]malononitrile were added and the mixture was stirred at 100° C. for 3 h. After this time, another 0.713 g (4.186 mmol) of [phenyldiazenyl]malononitrile was added, and the mixture was heated to 100° C. for 16 h. After cooling, the mixture was poured into water (800 ml) and ethyl acetate (300 ml). The organic phase was separated off and concentrated to dryness. The residue was triturated with ethyl acetate (200 ml) and filtered off with suction. The filter cake was washed with ethyl acetate and diethyl ether and dried under a high vacuum. This gave 4.60 g of the target compound (56% of theory, purity 74%).

LC-MS (method 2): $R_t$=0.99 min; MS (EIpos): m/z=440 $[M+H]^+$.

Example 9A

2-[7-(2-Fluorobenzyl)imidazo[1,5-b]pyridazin-5-yl]pyrimidine-4,5,6-triamine trihydrochloride

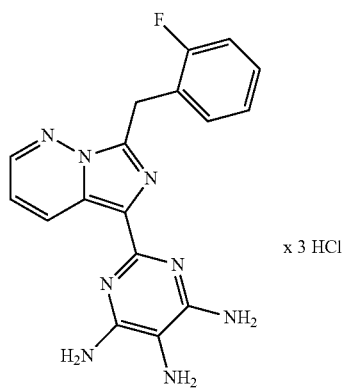 [SMILES: Nc1nc(-c2nc(Cc3ccccc3F)n3ncccc23)nc(N)c1N]

8.97 g (20.411 mmol) of the compound prepared in Example 8A were dissolved in DMF (1023 ml) and methanol (252 ml) and hydrogenated using 1.8 g of palladium on activated carbon (10%) at standard hydrogen pressure for 18 h. The mixture was then filtered through kieselguhr, the filter cake was washed with 400 ml of DMF and the filtrate was concentrated. 5 N hydrochloric acid (1000 ml) was added to the black evaporation residue, and the mixture was stirred for 1 h. The brown crystals formed were filtered off with suction and washed with water (50 ml) and diethyl ether (50 ml). The mother liquor was concentrated and then triturated with 1 N hydrochloric acid (200 ml). The precipitated crystals of the target product were washed with ethyl acetate (50 ml) and diethyl ether (50 ml). The crystals of the first precipitation were washed with ethyl acetate (2000 ml) and dichloromethan (1000 ml), combined with the other crystals and dried under high vacuum. This gave 5.03 g of the target compound in a purity of 90% (48% of theory).

LC-MS (method 2): $R_t$=0.75 min; MS (EIpos): m/z=351 $[M+H]^+$.

Example 10A

2-Chloroethyl {4,6-diamino-2-[7-(2-fluorobenzyl)imidazo[1,5-b]pyridazin-5-yl]pyrimidin-5-yl}carbamate

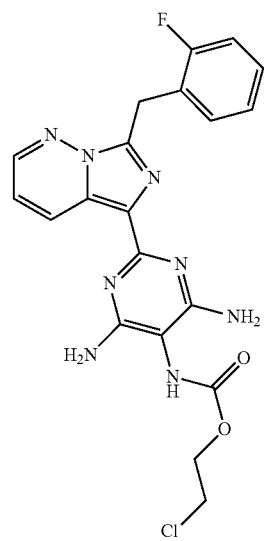 [SMILES: Nc1nc(-c2nc(Cc3ccccc3F)n3ncccc23)nc(N)c1NC(=O)OCCCl]

247 mg (0.623 mmol) of the compound prepared in Example 9A were initially charged in pyridine (2.5 ml) and dichloromethane (2.5 ml), 64 µl (0.623 mmol) of 2-chloroethyl chloroformate were added at 0° C. and the mixture was stirred at 0° C. for 10 min. After 16 hours of stirring at 20° C., another 64 µl (0.623 mmol) of 2-chloroethyl chloroformate were added, and the mixture was stirred at 20° C. for 16 hours. The reaction mixture was then poured onto ice-water and extracted twice with dichloromethane. The combined organic phases were dried over sodium sulfate, filtered and concentrated. The residue (314 mg) was used for the next step without further purification.

LC-MS (method 2): $R_t$=0.79 min; MS (EIpos): m/z=457 $[M+H]^+$.

Working Examples

Example 1

6-[7-(2-Fluorobenzyl)imidazo[1,5-b]pyridazin-5-yl]-1,3,5-triazine-2,4-diamine formate

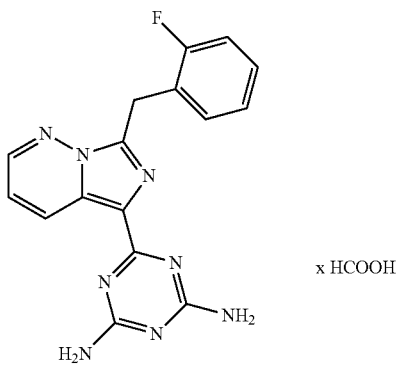 [SMILES: Nc1nc(N)nc(-c2nc(Cc3ccccc3F)n3ncccc23)n1]

100 mg (0.4 mmol) of 7-(2-fluorobenzyl)imidazo[1,5-b]pyridazine-5-carbonitrile (Example 6A) and 60 mg (0.71 mmol) of 1-cyanoguanidine in 1.3 ml of DMSO were stirred with 4.8 mg (0.12 mmol) of sodium hydroxide at 150° C. in a microwave reactor for 40 minutes. At 20° C., the reaction mixture was then diluted with ethyl acetate (50 ml) and washed twice with in each case 20 ml of water. Purification by HPLC (acetonitrile:water (+0.1% formic acid) gradient) and concentration of the product-containing fractions gave 37.2 mg (25% of theory) of the target compound.

LC-MS (method 2): $R_t$=0.73 min; MS (EIpos): m/z=337.3 [M+H]$^+$.

1H NMR (400 MHz, DMSO-$d_6$): δ [ppm]=4.47 (s, 2H), 6.40-6.92 (m br, 4H), 7.00 (dd, 1H), 7.10-7.25 (m, 2H), 7.25-7.35 (m, 2H), 8.11 (s, 0.5H), 8.42 (m, 1H), 9.00 (d, 1H), 12.76 (s br, 0.5H).

Example 2

Methyl {4,6-diamino-2-[7-(2-fluorobenzyl)imidazo[1,5-b]pyridazin-5-yl]pyrimidin-5-yl}carbamate formate

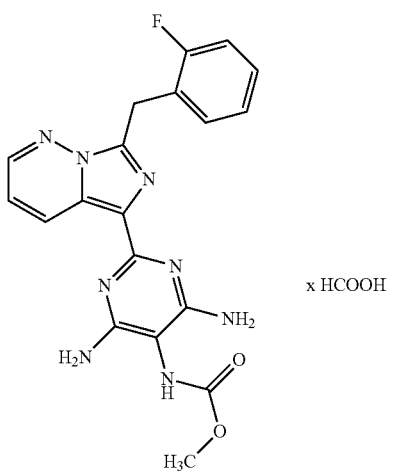 [SMILES: COC(=O)Nc1c(N)nc(-c2nc(Cc3ccccc3F)n3ncccc23)nc1N]

1.84 g (4.642 mmol) of the compound prepared in Example 9A were initially charged in pyridine (35 ml), 0.359 ml (4.642 mmol) of methyl chloroformate was added at 0° C. and the mixture was stirred at 0° C. for 10 min. After 16 hours of stirring at 20° C., the reaction mixture was poured into ice-water and extracted three times with ethyl acetate. The combined organic phases were washed with saturated aqueous sodium chloride solution, dried over sodium sulfate, filtered and concentrated. The residue was purified by chromatography on silica gel (mobile phase:gradient dichloromethane:methanol 100:5 to dichloromethane:methanol 2:1). This gave 1.13 g of the target compound (53% of theory).

LC-MS (method 2): $R_t$=0.74 min; MS (EIpos): m/z=409 [M+H]$^+$.

$^1$H NMR (400 MHz, DMSO-$d_6$): δ [ppm]=3.61 (s br, 3H), 4.48 (s, 2H), 6.05 (s br, 4H), 6.89 (dd, 1H), 7.11-7.33 (m, 4H), 7.94 (s br, 1H), 8.14 (s, 0.7H), 8.37 (dd, 1H), 9.02 (d, 1H).

Example 3

Isopropyl {4,6-diamino-2-[7-(2-fluorobenzyl)imidazo[1,5-b]pyridazin-5-yl]pyrimidin-5-yl}carbamate formate

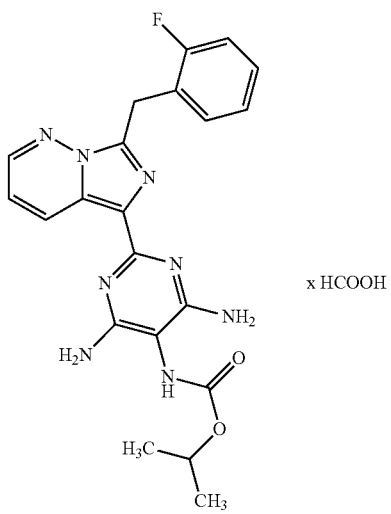 [SMILES: CC(C)OC(=O)Nc1c(N)nc(-c2nc(Cc3ccccc3F)n3ncccc23)nc1N]

At 0° C., twice at an interval of 10 minutes, in each case 76.4 mg (0.62 mmol) of isopropyl chloroformate were added to 247 mg (0.62 mmol) of 2-[7-(2-fluorobenzyl)imidazo[1,5-b]pyridazin-5-yl]pyrimidine-4,5,6-triamine (Example 9A) in 4.9 ml of pyridine. The reaction mixture was concentrated and the residue was purified by preparative HPLC (acetonitrile:water (+0.1% formic acid) gradient). This gave 189 mg (63% of theory) of the target compound.

LC-MS (method 1): $R_t$=1.63 min; MS (EIpos): m/z=437.2 [M+H]$^+$.

$^1$H NMR (400 MHz, DMSO-$d_6$): δ [ppm]=1.02-1.30 (broad signal, 6H), 4.48 (s, 2H), 4.80 (hept, 1H), 5.96 (s br, 4H), 6.88 (dd, 1H), 7.08-7.34 (m, 4H), 7.85 (s br, 1H), 8.12 (s, 2H), 8.36 (m, 1H), 9.02 (d, 1H), 12.70 (s br, 2H).

Example 4

Propyl 4,6-diamino-2-[7-(2-fluorobenzyl)imidazo[1,5-b]pyridazin-5-yl]pyrimidin-5-yl}carbamate formate

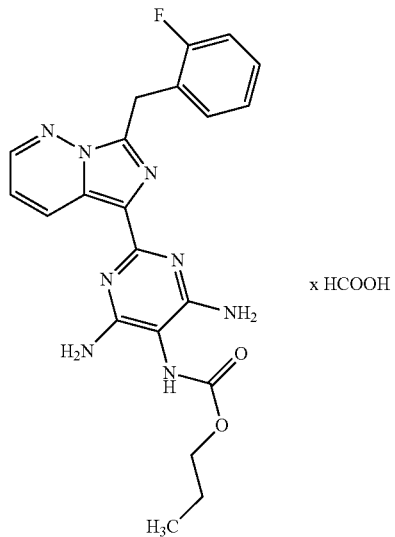 [SMILES: CCCOC(=O)Nc1c(N)nc(-c2nc(Cc3ccccc3F)n3ncccc23)nc1N]

x HCOOH

In analogy to Example 2, 150 mg (0.378 mmol) of Example 9A were reacted with 46.38 mg (0.378 mmol) of propyl chloroformate. The residue was purified by preparative HPLC (acetonitrile:water (+0.05% formic acid) gradient). This gave 24 mg of the target compound (11% of theory).

LC-MS (method 2): $R_t$=0.81 min; MS (EIpos): m/z=437 [M+H]$^+$.

$^1$H NMR (400 MHz, DMSO-$d_6$): δ [ppm]=0.75-1.02 (broad signal, 3H), 1.38-1.68 (broad signal, 2H), 3.97 (broad signal, 2H), 4.47 (s, 2H), 5.98 (s br, 4H), 6.88 (dd, 1H), 7.11-7.33 (m, 4H), 7.91 (s br, 1H), 8.14 (s, 0.5H), 8.36 (dd, 1H), 9.02 (d, 1H).

Example 5

Ethyl {4,6-diamino-2-[7-(2-fluorobenzyl)imidazo[1,5-b]pyridazin-5-yl]pyrimidin-5-yl}carbamate formate

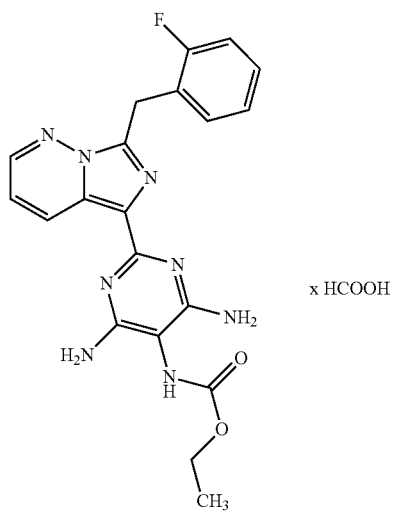 [SMILES: CCOC(=O)Nc1c(N)nc(-c2nc(Cc3ccccc3F)n3ncccc23)nc1N]

x HCOOH

In analogy to Example 2, 150 mg (0.378 mmol) of Example 9A were reacted with 41.07 mg (0.378 mmol) of ethyl chloroformate. The residue was purified by preparative HPLC (acetonitrile:water (+0.05% formic acid) gradient). This gave 18 mg of the target compound (9% of theory).

LC-MS (method 2): $R_t$=0.77 min; MS (EIpos): m/z=423 [M+H]$^+$.

$^1$H NMR (400 MHz, DMSO-$d_6$): δ [ppm]=1.23 (broad signal, 3H), 4.05 (broad signal, 2H), 4.47 (s, 2H), 5.99 (s br, 4H), 6.88 (dd, 1H), 7.11-7.33 (m, 4H), 7.90 (s br, 1H), 8.14 (s, 0.9H), 8.37 (dd, 1H), 9.02 (d, 1H).

Example 6

2-Fluoroethyl-{4,6-diamino-2-[7-(2-fluorobenzyl)imidazo[1,5-b]pyridazin-5-yl]pyrimidin-5-yl}carbamate formate

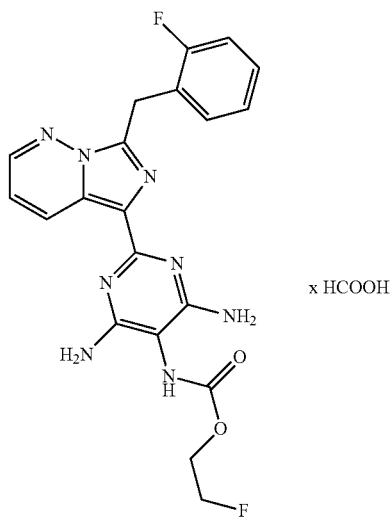 [SMILES: Nc1nc(-c2nc(Cc3ccccc3F)n3ncccc23)nc(N)c1NC(=O)OCCF]

x HCOOH

At 0° C., 32 mg (0.25 mmol) of 2-fluoroethyl chloroformate were added to 100 mg (0.25 mmol) of 2-[7-(2-fluorobenzyl)imidazo[1,5-b]pyridazin-5-yl]pyrimidine-4,5,6-triamine (Example 9A) in 2 ml of pyridine and stirred at 0° C. for 1.5 hours. The reaction mixture was concentrated and the residue was purified by preparative HPLC (acetonitrile:water (+0.1% formic acid) gradient). This gave 39 mg (31% of theory) of the target compound.

LC-MS (method 2): $R_t$=0.76 min; MS (EIpos): m/z=441.1 [M+H]$^+$.

$^1$H NMR (400 MHz, DMSO-$d_6$): δ [ppm]=4.21, 4.30 (2 s br, 2×1H), 4.48 (s, 2H), 4.60, 4.72 (2 s br, 2×1H), 6.02 (s br, 4H), 6.88 (dd, 1H), 7.07-7.37 (m, 4H), 7.82 (s br, 1H), 8.09 (s, 1H), 8.12 (s, 2H), 8.37 (m, 1H), 9.01 (d, 1H), 12.70 (s br, 1H).

Example 7

Cyclopentyl {4,6-diamino-2-[7-(2-fluorobenzyl)imidazo[1,5-b]pyridazin-5-yl]pyrimidin-5-yl}carbamate formate

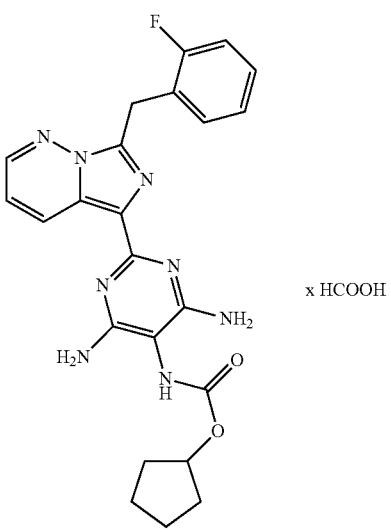 [SMILES: Nc1nc(-c2nc(Cc3ccccc3F)n3ncccc23)nc(N)c1NC(=O)OC1CCCC1]

At 0° C., 37.5 mg (0.25 mmol) of cyclopentyl chlorocarbonate were added to 100 mg (0.25 mmol) of 2-[7-(2-fluorobenzyl)imidazo[1,5-b]pyridazin-5-yl]pyrimidine-4,5,6-triamine (Example 9A) in 2 ml of pyridine. The reaction mixture was concentrated and the residue was purified by preparative HPLC (acetonitrile:water (+0.1% formic acid) gradient). This gave 41 mg (32% of theory) of the target compound.

LC-MS (method 2): $R_t$=0.87 min; MS (EIpos): m/z=463.1 [M+H]$^+$.

$^1$H NMR (400 MHz, DMSO-d$_6$): δ [ppm]=1.40-1.89 (m, br, 8H), 4.48 (s, 2H), 5.00 (s br, 1H), 5.95 (s br, 4H), 6.88 (dd, 1H), 7.10-7.35 (m, 4H), 7.82 (s br, 1H), 8.14 (s, 1H), 8.37 (m, 1H), 9.01 (d, 1H), 12.70 (s br, 1H).

Example 8

Methyl {4,6-diamino-2-[7-(2-fluorobenzyl)imidazo [1,5-b]pyridazin-5-yl]pyrimidin-5-yl}ethylcarbamate formate

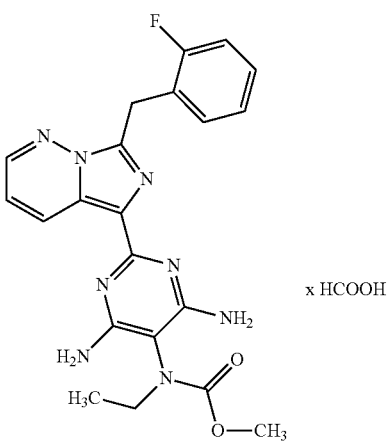 [SMILES: CCN(C(=O)OC)c1c(N)nc(-c2nc(Cc3ccccc3F)n3ncccc23)nc1N]

At 0° C., 400 mg (0.979 mmol) of Example 2 were initially charged in THF (5 ml), and 1.077 ml (1.077 mmol) of sodium bis(trimethylsilyl)amide (1 M in THF) were added. After 30 min at 0° C., 0.157 ml (1.959 mmol) of ethyl iodide was added and the mixture was stirred at 20° C. for 16 hours. The reaction mixture was then poured onto water and extracted with ethyl acetate. The phases were separated and the aqueous phase was extracted twice with ethyl acetate. The combined organic phases were washed with saturated aqueous sodium chloride solution, dried over sodium sulfate, filtered and concentrated. The residue was purified by preparative HPLC (acetonitrile:water (+0.05% formic acid) gradient). This gave 209 mg of the target compound (44% of theory).

LC-MS (method 2): $R_t$=0.79 min; MS (EIpos): m/z=437 [M+H]$^+$.

$^1$H NMR (400 MHz, DMSO-d$_6$): δ [ppm]=1.05 (t, 3H), 3.47 (q, 2H), 3.53 and 3.66 (2s br, together 3H), 4.48 (s, 2H), 6.18 (s br, 4H), 6.88 (dd, 1H), 7.10-7.32 (m, 4H), 8.14 (s, 0.6H), 8.37 (dd, 1H), 9.03 (d, 1H).

Example 9

Methyl {4,6-diamino-2-[7-(2-fluorobenzyl)imidazo [1,5-b]pyridazin-5-yl]pyrimidin-5-yl}methylcarbamate formate

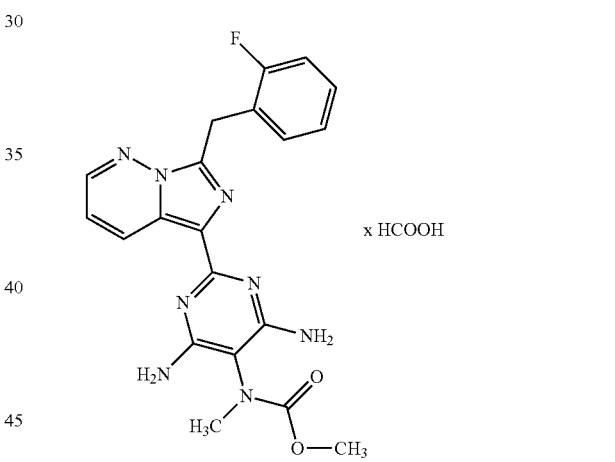

At 0° C., 100 mg (0.22 mmol) of methyl {4,6-diamino-2-[7-(2-fluorobenzyl)imidazo[1,5-b]pyridazin-5-yl]pyrimidin-5-yl}carbamate formate were initially charged in THF (0.94 ml), and 44.4 mg (0.24 mmol) of a 2 N solution of sodium bis(trimethylsilyl)amide in THF were added. After 30 min at 0° C., 27 μl (0.22 mmol) of methyl iodide were added and the mixture was stirred at 20° C. for 20 hours. The mixture was then concentrated and the residue was purified by preparative HPLC (acetonitrile:water (+0.1% formic acid) gradient). This gave 31 mg of the target compound in a purity of 100% (HPLC) (33% of theory).

LC-MS (method 2): $R_t$=0.80 min; MS (EIpos): m/z=423.1 [M+H]$^+$.

$^1$H NMR (400 MHz, DMSO-d$_6$): δ [ppm]=2.98 (s, 3H), 3.50 and 3.64 (2s, together 3H), 4.48 (s, 3H), 6.20 (s br, 4H), 6.88 (dd, 1H), 7.01-7.35 (m, 4H), 8.14 (s, 0.6H), 8.35 (m, 1H), 9.01 (d, 1H), 12.70 (s br, 1H).

Example 10

Methyl {4,6-diamino-2-[7-(2-fluorobenzyl)imidazo[1,5-b]pyridazin-5-yl]pyrimidin-5-yl}(2,2,2-trifluoroethyl)

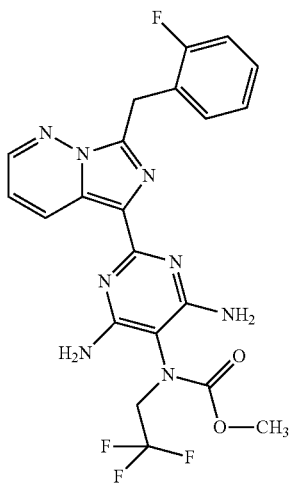 [SMILES: COC(=O)N(CC(F)(F)F)c1c(N)nc(-c2nc(Cc3ccccc3F)n3ncccc23)nc1N]

At 0° C., 150 mg (0.330 mmol) of the compound prepared in Example 2 were initially charged in THF (3 ml), and 14 mg (0.363 mmol) of sodium hydride (60% in mineral oil) were added. After 30 min at 0° C., 63 µl (0.363 mmol) of 2,2,2-trifluoroethyl trichloromethanesulfonate were added, and the mixture was stirred at 20° C. for 3 days. At 20° C., another 14 mg (0.363 mmol) of sodium hydride (60% in mineral oil) were then added, followed 30 min later by 63 µl (0.363 mmol) of 2,2,2-trifluoroethyl trichloromethanesulfonate, and the mixture was stirred at 20° C. for 16 hours. The next day, another 14 mg (0.363 mmol) of sodium hydride (60% in mineral oil) were added, followed 30 min later by 63 µl (0.363 mmol) of 2,2,2-trifluoroethyl trichloromethanesulfonate, and the mixture was stirred at 20° C. for 16 hours. Water was then added, and the mixture was stirred for 15 min and concentrated. The residue was purified by preparative HPLC (acetonitrile:water (+0.05% formic acid) gradient). This gave 11 mg of the target compound (6% of theory).

LC-MS (method 2): $R_t$=0.86 min; MS (EIpos): m/z=491 [M+H]$^+$.

$^1$H NMR (400 MHz, DMSO-d$_6$): δ [ppm]=3.62 and 3.72 (2s br, together 3H), 4.05-4.20 (m, 2H), 4.48 (s, 2H), 6.24 (s br, 4H), 6.90 (dd, 1H), 7.10-7.32 (m, 4H), 8.38 (dd, 1H), 9.03 (d, 1H).

Example 11

Cyclobutyl {4,6-diamino-2-[7-(2-fluorobenzyl)imidazo[1,5-b]pyridazin-5-yl]pyrimidin-5-yl}carbamate formate

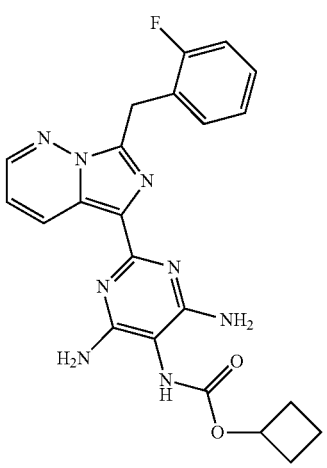

42 mg (0.14 mmol) of bis(trichloromethyl)carbonate were added to 27.3 mg (0.38 mmol) of cyclobutanol, and the mixture was cooled to 0° C. At this temperature, 31 µl (0.38 mmol) of pyridine were added slowly, and the mixture was then stirred at 20° C. for one hour. The mixture was then cooled again to 0° C., and a solution of 100 mg (0.25 mmol) of 2-[7-(2-fluorobenzyl)imidazo[1,5-b]pyridazin-5-yl]pyrimidine-4,5,6-triamine (Example 9A) in 1 ml of pyridine was added. The reaction mixture was stirred in an ice bath for 10 minutes, and 2 ml of saturated aqueous sodium bicarbonate solution were then added. The concentrated reaction was purified by preparative HPLC (acetonitrile:water (+0.1% formic acid) gradient). This gave 25 mg (20% of theory) of the target compound.

LC-MS (method 2): $R_t$=0.83 min; MS (EIpos): m/z=449.1 [M+H]$^+$.

$^1$H NMR (400 MHz, DMSO-d$_6$): δ [ppm]=1.55, 1.71 (2m, 2×1H), 2.06, 2.25 (2m, 2×2H), 4.46 (s, 2H), 4.85 (m, 1H), 6.0 (s br, 4H), 6.88 (dd, 1H), 7.05-7.40 (m, 4H), 7.90 (s, 1H), 8.14 (s, 1H), 8.35 (m, 1H), 9.02 (d, 1H), 12.70 (s br, 1H).

Example 12

Isobutyl {4,6-diamino-2-[7-(2-fluorobenzyl)imidazo[1,5-b]pyridazin-5-yl]pyrimidin-5-yl}carbamate formate

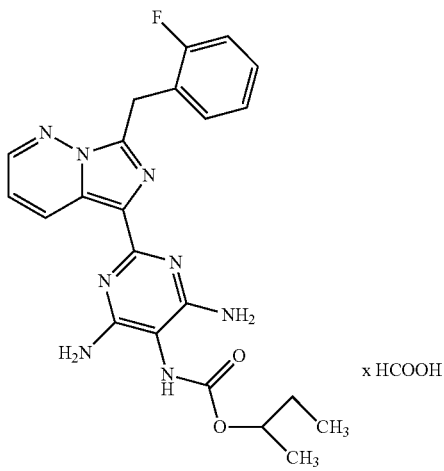 [SMILES: CCC(C)OC(=O)Nc1c(N)nc(-c2nc(Cc3ccccc3F)n3ncccc23)nc1N ; "x HCOOH"]

Analogously to Example 11, 28 mg (0.38 mmol) of 2-butanol gave 36 mg (28% of theory) of the target compound.

LC-MS (method 2): $R_t$=0.86 min; MS (EIpos): m/z=451.1 [M+H]$^+$.

$^1$H NMR (400 MHz, DMSO-d$_6$): δ [ppm]=0.72-0.95, 1.02-1.28 (2m br, 2×3H), 1.30-1.70 (m br, 2H), 4.46 (s, 2H), 4.63 (m, 1H), 5.96 (s br, 4H), 6.89 (dd, 1H), 7.05-7.40 (m, 4H), 7.89 (s br, 1H), 8.12 (s, 1H), 8.37 (m, 1H), 9.02 (d, 1H), 12.70 (s br, 1H).

Example 13

N-{4,6-Diamino-2-[7-(2-fluorobenzyl)imidazo[1,5-b]pyridazin-5-yl]pyrimidin-5-yl}propanamide formate

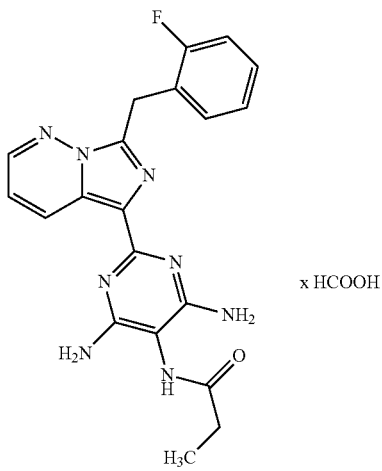 [SMILES: CCC(=O)Nc1c(N)nc(-c2nc(Cc3ccccc3F)n3ncccc23)nc1N ; "x HCOOH"]

200 mg (0.51 mmol) of the compound prepared in Example 9A were initially charged in pyridine (9.3 ml), 44 μl (0.51 mmol) of propionyl chloride were added and the mixture was stirred at 20° C. for 18 hours. The crude mixture was purified by preparative HPLC (acetonitrile/water gradient+0.1% formic acid). This gave 111 mg (47% of theory, purity 98%) of the target compound.

LC-MS (method 2): $R_t$=0.71 min; MS (EIpos): m/z=407 [M+H]$^+$.

Example 14

N-{4,6-Diamino-2-[7-(2-fluorobenzyl)imidazo[1,5-b]pyridazin-5-yl]pyrimidin-5-yl}-N-methylpropanamide formate

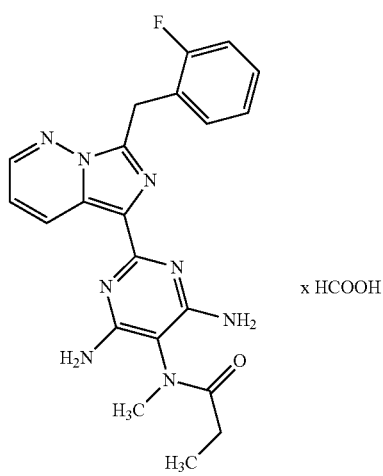 [SMILES: CCC(=O)N(C)c1c(N)nc(-c2nc(Cc3ccccc3F)n3ncccc23)nc1N ; "x HCOOH"]

At 0° C., 50 mg (0.11 mmol) of N-{4,6-diamino-2-[7-(2-fluorobenzyl)imidazo[1,5-b]pyridazin-5-yl]pyrimidin-5-yl}propanamide formate were initially charged in THF (0.47 ml), and 22.3 mg of a 2 N solution of sodium bis(trimethylsilyl)amide in THF (0.12 mmol) were added. After 30 min at 0° C., 14 μl (0.22 mmol) of methyl iodide were added and the mixture was stirred at 20° C. for 20 hours. The mixture was then concentrated and the residue was purified by preparative HPLC (acetonitrile/water (+0.1% formic acid) gradient). This gave 17 mg of the target compound (32% of theory).

LC-MS (method 2): $R_t$=0.80 min; MS (EIpos): m/z=421.1 [M+H]$^+$.

$^1$H NMR (400 MHz, DMSO-d$_6$): δ [ppm]=0.93 (t, 3H), 2.01 (q, 2H), 2.98 (s, 3H), 4.48 (s, 2H), 6.33 (s br, 4H), 6.89 (dd, 1H), 7.08-7.34 (m, 4H), 8.12 (s, 1H), 8.37 (m, 1H), 9.03 (d, 1H), 12.74 (s br, 1H).

Example 15

Methyl benzyl{4,6-diamino-2-[7-(2-fluorobenzyl)imidazo[1,5-b]pyridazin-5-yl]pyrimidin-5-yl}carbamate formate

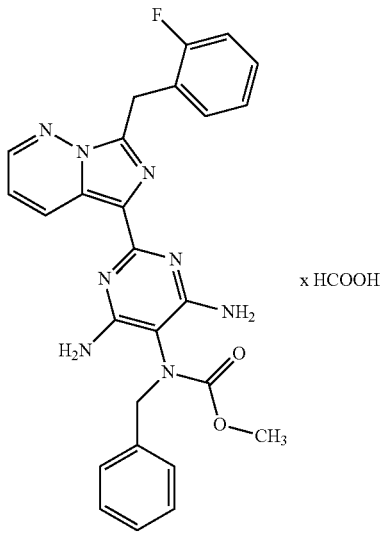 [SMILES: COC(=O)N(Cc1ccccc1)c1c(N)nc(-c2nc(Cc3ccccc3F)n3ncccc23)nc1N ; "x HCOOH"]

At 0° C., 100 mg (0.22 mmol) of methyl {4,6-diamino-2-[7-(2-fluorobenzyl)imidazo[1,5-b]pyridazin-5-yl]pyrimidin-5-yl}carbamate formate were initially charged in THF (0.94 ml), and 44.4 mg (0.24 mmol) of a 2 N solution of sodium bis(trimethylsilyl)amide in THF were added. After 30 min at 0° C., 52 μl (0.44 mmol) of benzyl bromide were added and the mixture was stirred at 20° C. for 20 hours. The reaction mixture was then concentrated and the residue was purified by preparative HPLC (acetonitrile/water (+0.1% formic acid) gradient). This gave 105 mg of the target compound (87% of theory).

LC-MS (method 2): $R_t$=0.88 min; MS (EIpos): m/z=499.2 [M+H]$^+$.

$^1$H NMR (400 MHz, DMSO-d$_6$): δ [ppm]=3.59 and 3.74 (2s, br, together 3H), 4.45 (s, 2H), 4.58 (s br, 1H), 5.91 (s br, 4H), 6.83 (dd, 1H), 7.08-7.40 (m, 9H), 8.12 (s, 1H), 8.35 (m, 1H), 8.97 (d, 1H), 12.80 (s br, 1H).

Example 16

Propyl {4,6-diamino-2-[7-(2-fluorobenzyl)imidazo[1,5-b]pyridazin-5-yl]pyrimidin-5-yl}methylcarbamate formate

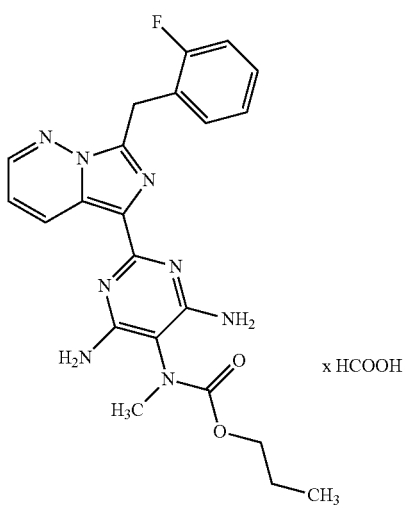 [SMILES: CCCOC(=O)N(C)c1c(N)nc(-c2nc(Cc3ccccc3F)n3ncccc23)nc1N ; "x HCOOH"]

At 0° C., 182 mg (0.38 mmol) of propyl {4,6-diamino-2-[7-(2-fluorobenzyl)imidazo[1,5-b]pyridazin-5-yl]pyrimidin-5-yl}carbamate were initially charged in THF (1.6 ml), and 76.2 mg (0.42 mmol) of a 2 N solution of sodium bis(trimethylsilyl)amide in THF were added. After 30 min at 0° C., 47 μl (0.76 mmol) of methyl iodide were added and the mixture was stirred at 20° C. for 20 hours. The mixture was then concentrated and the residue was purified by preparative HPLC (acetonitrile/water (+0.1% formic acid) gradient). This gave 21 mg of the target compound (12% of theory, purity 93%).

LC-MS (method 2): $R_t$=0.86 min; MS (EIpos): m/z=451.1 [M+H]$^+$.

$^1$H NMR (400 MHz, DMSO-d$_6$): δ [ppm]=0.76 and 0.95 (2t, together 3H), 1.45 and 1.63 (2q, together 2H), 3.00 and 3.18 (2s, together 3H), 3.90 and 3.98 (2t, together 2H), 4.46 and 4.55 (2s, together 2H), 6.16 (s br, 4H), 6.88 (dd, 1H), 7.01-7.75 (peak cluster, >5H), 8.14 (s, 1H), 8.37 (dd, 1H), 9.03 (d, 1H), 12.70 (s br, 1H).

Example 17

Ethyl {4,6-diamino-2-[7-(2-fluorobenzyl)imidazo[1,5-b]pyridazin-5-yl]pyrimidin-5-yl}methylcarbamate formate

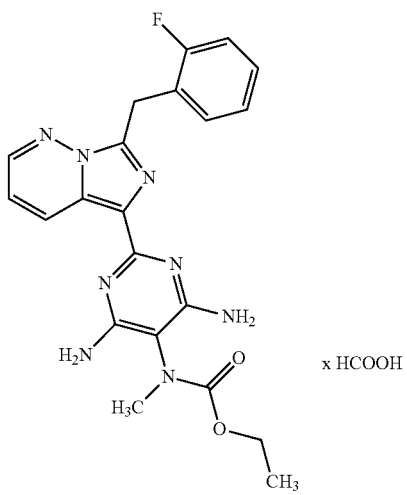 [SMILES: CCOC(=O)N(C)c1c(N)nc(-c2nc(Cc3ccccc3F)n3ncccc23)nc1N ; "x HCOOH"]

At 0° C., 177 mg (0.42 mmol) of ethyl {4,6-diamino-2-[7-(2-fluorobenzyl)imidazo[1,5-b]pyridazin-5-yl]pyrimidin-5-yl}carbamate were initially charged in THF (1.8 ml), and 84.5 mg (0.46 mmol) of a 2 N solution of sodium bis(trimethylsilyl)amide in THF were added. After 30 min at 0° C., 52 μl (0.84 mmol) of methyl iodide were added and the mixture was stirred at 20° C. for 20 hours. The mixture was then concentrated and the residue was purified by preparative HPLC (acetonitrile/water (+0.1% formic acid) gradient). This gave 37 mg of the target compound (20% of theory).

LC-MS (method 2): $R_t$=0.82 min; MS (EIpos): m/z=437.1 [M+H]$^+$.

$^1$H NMR (400 MHz, DMSO-d$_6$): δ [ppm]=1.09 and 1.25 (2t, together 3H), 3.00 (s, 3H), 4.00 and 4.08 (2q, together 2H), 4.48 (s, 2H), 6.15 (s br, 4H), 6.88 (dd, 1H), 7.05-7.65 (peak cluster, 4H), 8.12 (s, 1H), 8.37 (m, 1H), 9.01 (d, 1H), 12.70 (s br, 1H).

Example 18

Methyl {4,6-diamino-2-[7-(2-fluorobenzyl)imidazo[1,5-b]pyridazin-5-yl]pyrimidin-5-yl}(2-fluorobenzyl)carbamate formate

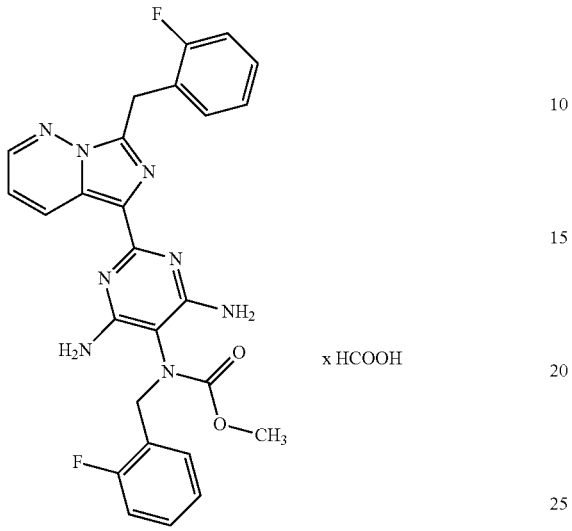

80 mg (0.196 mmol) of Example 2 were reacted analogously to Example 8 with 74 mg (0.392 mmol) of 2-fluorobenzyl bromide. This gave 77 mg of the target compound (70% of theory).

LC-MS (method 2): $R_t$=0.90 min; MS (EIpos): m/z=517 [M+H]$^+$.

$^1$H NMR (400 MHz, DMSO-d$_6$): δ [ppm]=3.59 and 3.74 (2s br, together 3H), 4.46 (s, 2H), 4.69 (s, 2H), 5.96 (s br, 4H), 6.86 (dd, 1H), 7.05-7.32 (m, 7H), 7.53 (t, 1H), 8.14 (s, 0.4H), 8.35 (dd, 1H), 8.98 (d, 1H).

Example 19

Methyl {4,6-diamino-2-[7-(2-fluorobenzyl)imidazo[1,5-b]pyridazin-5-yl]pyrimidin-5-yl}(3-fluorobenzyl)carbamate formate

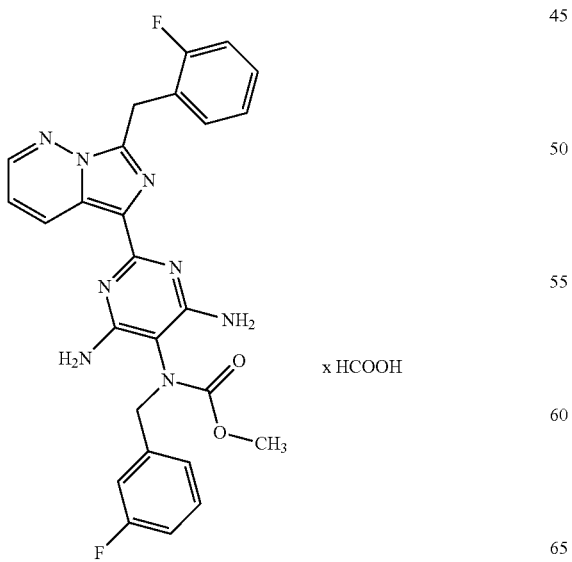

80 mg (0.196 mmol) of Example 2 were reacted analogously to Example 8 with 74 mg (0.392 mmol) of 3-fluorobenzyl bromide. This gave 49 mg of the target compound (44% of theory).

LC-MS (method 2): $R_t$=0.92 min; MS (EIpos): m/z=517 [M+H]$^+$.

$^1$H NMR (400 MHz, DMSO-d$_6$): δ [ppm]=3.60 and 3.74 (2s br, together 3H), 4.45 (s, 2H), 4.60 (s, 2H), 6.02 (s br, 4H), 6.85 (dd, 1H), 7.03-7.32 (m, 8H), 8.14 (s, 0.3H), 8.35 (dd, 1H), 8.97 (d, 1H).

Example 20

Methyl {4,6-diamino-2-[7-(2-fluorobenzyl)imidazo[1,5-b]pyridazin-5-yl]pyrimidin-5-yl}(4-fluorobenzyl)carbamate formate

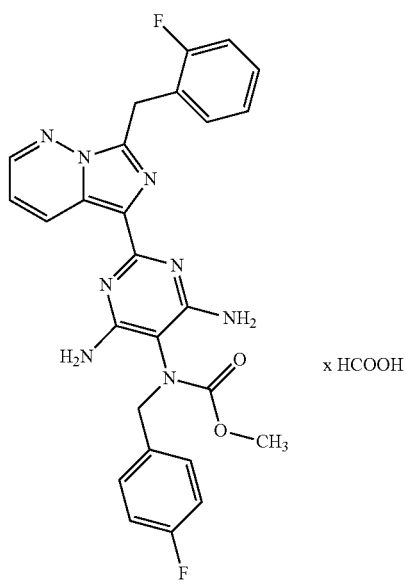 [SMILES: COC(=O)N(Cc1ccc(F)cc1)c1c(N)nc(-c2nc(Cc3ccccc3F)n3ncccc23)nc1N ; "x HCOOH"]

80 mg (0.196 mmol) of Example 2 were reacted analogously to Example 8 with 74 mg (0.392 mmol) of 4-fluorobenzyl bromide. This gave 40 mg of the target compound (36% of theory).

LC-MS (method 2): $R_t$=0.91 min; MS (EIpos): m/z=517 [M+H]$^+$.

$^1$H NMR (400 MHz, DMSO-d$_6$): δ [ppm]=3.58 and 3.74 (2s br, together 3H), 4.45 (s, 2H), 4.57 (s, 2H), 5.97 (s br, 4H), 6.86 (dd, 1H), 7.03-7.41 (m, 8H), 8.14 (s, 0.3H), 8.35 (dd, 1H), 8.97 (d, 1H).

Example 21

3-{4,6-Diamino-2-[7-(2-fluorobenzyl)imidazo[1,5-b]pyridazin-5-yl]pyrimidin-5-yl}-1,3-oxazolidin-2-one formate

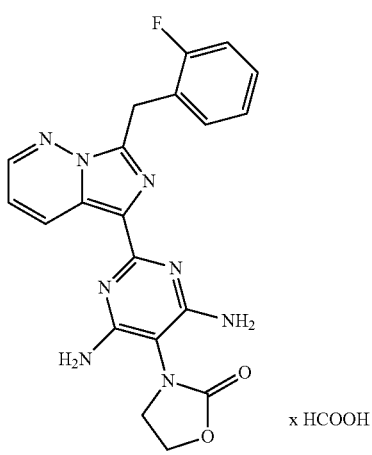 [SMILES: Nc1nc(-c2nc(Cc3ccccc3F)n3ncccc23)nc(N)c1N1CCOC1=O ; "x HCOOH"]

x HCOOH

At 0° C., 314 mg (about 0.687 mmol) of Example 10A were initially charged in THF (10 ml), and 0.687 ml (0.687 mmol) of a 1 M solution of sodium bis(trimethylsilyl)amide in THF was added. After 30 min at 0° C., the reaction mixture was stirred at 20° C. for 30 min The reaction mixture was then poured onto water and extracted with ethyl acetate. The phases were separated and the aqueous phase was extracted twice with ethyl acetate. The combined organic phases were washed with saturated aqueous sodium chloride solution, dried over sodium sulfate, filtered and concentrated. The residue was purified by preparative HPLC (methanol:water (+0.05% formic acid) gradient). This gave 57 mg of the target compound (19% of theory).

LC-MS (method 2): $R_t$=0.73 min; MS (EIpos): m/z=421 [M+H]$^+$.

$^1$H NMR (400 MHz, DMSO-d$_6$): δ [ppm]=3.64 (t, 2H), 4.41 (t, 2H), 4.48 (s, 2H), 6.47 (s br, 4H), 6.90 (dd, 1H), 7.11-7.33 (m, 4H), 8.15 (s, 0.7H), 8.38 (dd, 1H), 9.02 (d, 1H).

B. ASSESSMENT OF PHARMACOLOGICAL EFFICACY

The pharmacological effect of the compounds according to the invention can be shown in the following assays:

B-1. Vasorelaxant Action In Vitro

Rabbits are stunned by a blow to the neck and exsanguinated. The aorta is removed, freed from adhering tissue and divided into rings of a width of 1.5 mm. The rings are placed individually under an initial tension in 5 ml organ baths with Krebs-Henseleit solution which is at 37° C., is gassed with carbogen and has the following composition (in each case mM): sodium chloride 119; potassium chloride: 4.8; calcium chloride dihydrate: 1; magnesium sulfate heptahydrate: 1.4; potassium dihydrogenphosphate: 1.2; sodium bicarbonate: 25; glucose: 10. The contractile force is determined with Statham UC$_2$ cells, amplified and digitalized using A/D transducers (DAS 1802 HC, Keithley Instruments Munich), and recorded in parallel on linear recorders. To obtain a contraction, phenylephrine is added to the bath cumulatively in increasing concentration. After several control cycles, the substance to be investigated is added in each further run in increasing dosage in each case, and the height of the contraction achieved is compared with the height of the contraction reached in the last preceding run. This is used to calculate the concentration needed to reduce the magnitude of the control value by 50% (IC$_{50}$ value). The standard administration volume is 5 μl; the DMSO content in the bath solution corresponds to 0.1%.

Representative IC$_{50}$ values for the compounds according to the invention are shown in the table below (Table 1):

TABLE 1

| Example No. | IC$_{50}$ [nM] |
|---|---|
| 1 | 130 |
| 5 | 200 |
| 8 | 152 |
| 11 | 422 |
| 15 | 171 |
| 19 | 81 |

B-2. Effect on a Recombinant Guanylate Cyclase Reporter Cell Line

The cellular activity of the compounds according to the invention is determined using a recombinant guanylate cyclase reporter cell line, as described in F. Wunder et al., Anal. Biochem. 339, 104-112 (2005).

Representative values (MEC=minimum effective concentration) for the compounds according to the invention are shown in the table below (Table 2):

TABLE 2

| Example No. | MEC [μM] |
|---|---|
| 1 | 0.03 |
| 5 | 0.3 |
| 8 | 0.1 |
| 11 | 0.3 |
| 15 | 0.01 |
| 19 | 0.1 |

B-3. Radiotelemetric Measurement of Blood Pressure on Conscious Spontaneously Hypertensive Rats A commercially available telemetry system from DATA SCIENCES INTERNATIONAL DSI, USA, is employed for the blood pressure measurement on conscious rats described below.

The system consists of 3 main components:
implantable transmitters (Physiotel® telemetry transmitter)
receivers (Physiotel® receiver) which are linked via a multiplexer (DSI Data Exchange Matrix) to a
data acquisition computer.

The telemetry system makes it possible to continuously record blood pressure, heart rate and body motion of conscious animals in their usual habitat.

Animal Material

The investigations are carried out on adult female spontaneously hypertensive rats (SHR Okamoto) with a body weight of >200 g. SHR/NCrl from the Okamoto Kyoto School of Medicine, 1963 were a cross of male Wistar Kyoto rats with highly elevated blood pressure and female rats having a slightly elevated blood pressure and at F13 handed over to the U.S. National Institutes of Health.

After transmitter implantation, the experimental animals are housed singly in type 3 Makrolon cages. They have free access to standard feed and water.

The day/night rhythm in the experimental laboratory is changed by the room lighting at 6.00 am and at 7.00 pm.
Transmitter Implantation The telemetry transmitters TA11 PA-C40 used are surgically implanted under aseptic conditions in the experimental animals at least 14 days before the first experimental use. The animals instrumented in this way can be employed repeatedly after the wound has healed and the implant has settled.

For the implantation, the fasted animals are anesthetized with pentobarbital (Nembutal, Sanofi: 50 mg/kg i.p.) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (VetBonD™, 3M). The transmitter housing is fixed intraperitoneally to the abdominal wall muscle, and the wound is closed layer by layer.

An antibiotic (Tardomyocel COMP, Bayer, 1 ml/kg s.c.) is administered postoperatively for prophylaxis of infection.
Substances and Solutions Unless indicated otherwise, the substances to be investigated are administered orally by gavage in each case to a group of animals (n=6). The test substances are dissolved in suitable solvent mixtures, or suspended in 0.5% strength Tylose, appropriate for an administration volume of 5 ml/kg of body weight.

A solvent-treated group of animals is employed as control.
Test Procedure

The telemetry measuring unit present is configured for 24 animals. Each experiment is recorded under an experiment number (Vyear month day).

Each of the instrumented rats living in the system is assigned a separate receiving antenna (1010 Receiver, DSI).

The implanted transmitters can be activated externally by means of an incorporated magnetic switch and are switched to transmission in the run-up to the experiment. The emitted signals can be detected online by a data acquisition system (Dataquest™ A.R.T. for Windows, DSI) and be appropriately processed. The data are stored in each case in a file created for this purpose and bearing the experiment number.

In the standard procedure, the following are measured for 10-second periods in each case:
systolic blood pressure (SBP)
diastolic blood pressure (DBP)
mean arterial pressure (MAP)
heart rate (HR)
activity (ACT).

The acquisition of measured values is repeated under computer control at 5-minute intervals. The source data obtained as absolute value are corrected in the diagram with the currently measured barometric pressure (Ambient Pressure Reference Monitor; APR-1) and stored as individual data. Further technical details are given in the extensive documentation from the manufacturing company (DSI).

Unless indicated otherwise, the test substances are administered at 9.00 am on the day of the experiment. Following the administration, the parameters described above are measured over 24 hours.
Evaluation After the end of the experiment, the acquired individual data are sorted using the analysis software (Dataquest™ A.R.T.™ Analysis). The blank value is assumed to be the time 2 hours before administration, and so the selected data set encompasses the period from 7.00 am on the day of the experiment to 9.00 am the following day.

The data are smoothed over a presettable time by determination of the average (15-minute average) and transferred as a text file to a storage medium. The measured values presorted and compressed in this way are transferred into Excel templates and tabulated. For each day of the experiment, the data obtained are stored in a dedicated file carrying the number of the experiment. Results and test protocols are filed in paper form sorted by numbers.
Literature Klaus Witte, Kai Hu, Johanna Swiatek, Claudia Müssig, Georg Ertl and Björn Lemmer: Experimental heart failure in rats: effects on cardiovascular circadian rhythms and on myocardial β-adrenergic signaling. Cardiovasc Res 47 (2): 203-405, 2000; Kozo Okamoto: Spontaneous hypertension in rats. Int Rev Exp Pathol 7: 227-270, 1969; Maarten van den Buuse: Circadian Rhythms of Blood Pressure, Heart Rate, and Locomotor Activity in Spontaneously Hypertensive Rats as Measured With Radio-Telemetry. Physiology & Behavior 55(4): 783-787, 1994

C. WORKING EXAMPLES OF PHARMACEUTICAL COMPOSITIONS

The compounds according to the invention can be converted to pharmaceutical formulations as follows:
Tablet:
Composition:

100 mg of the compound according to the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg, diameter 8 mm, radius of curvature 12 mm.
Production:

The mixture of the compound according to the invention, lactose and starch is granulated with a 5% solution (w/w) of the PVP in water. The granules are dried and mixed with the magnesium stearate for 5 minutes. This mixture is pressed with a conventional tableting press (for tablet dimensions see above). The guide value used for the pressing is a pressing force of 15 kN.
Suspension which can be Administered Orally:
Composition:

1000 mg of the compound according to the invention, 1000 mg of ethanol (96%), 400 mg of Rhodigel® (xanthan gum from FMC, Pennsylvania, USA) and 99 g of water.

A single dose of 100 mg of the compound according to the invention corresponds to 10 ml of oral suspension.
Production:

The Rhodigel is suspended in ethanol and the compound according to the invention is added to the suspension. The water is added while stirring. The mixture is stirred for about 6 h until swelling of the Rhodigel is complete.
Solution which can be Administered Orally:
Composition:

500 mg of the compound according to the invention, 2.5 g of polysorbate and 97 g of polyethylene glycol 400. A single dose of 100 mg of the compound according to the invention corresponds to 20 g of oral solution.
Production:

The compound according to the invention is suspended in the mixture of polyethylene glycol and polysorbate while stirring. The stirring operation is continued until dissolution of the compound according to the invention is complete.
i.v. Solution:

The compound according to the invention is dissolved in a concentration below the saturation solubility in a physiologically acceptable solvent (e.g. isotonic saline, glucose solution 5% and/or PEG 400 solution 30%). The solution is subjected to sterile filtration and dispensed into sterile and pyrogen-free injection vessels.

The invention claimed is:
1. A compound of formula (I)

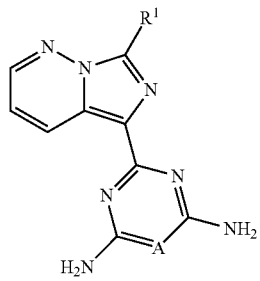

in which
R¹ is 2-fluorobenzyl,
A is C—N(R²)—C(=O)—R³,
where
R² is hydrogen, methyl, ethyl or 2,2,2-trifluoroethyl,
R³ is $(C_1$-$C_4)$-alkoxy, cyclobutoxy or cyclopentoxy,
in which $(C_1$-$C_4)$-alkoxy may be substituted by 1 or 2 substituents independently of one another selected from the group consisting of fluorine and trifluoromethyl,
or
R² and R³ together with the atoms to which they are attached form a pyrrolidinonyl or oxazolidinonyl ring,
or a pharmaceutically acceptable salt thereof.

2. A pharmaceutical composition comprising a compound of claim 1 and an inert, nontoxic, pharmaceutically suitable excipient.

3. A method for the treatment of hypertension and pulmonary hypertension comprising administering to a human or animal in need thereof an effective amount of at least one compound of claim 1.

4. A method for the treatment of hypertension and pulmonary hypertension comprising administering to a human or animal in need thereof an effective amount of the pharmaceutical composition of claim 2.

* * * * *